(12) United States Patent
Lefebvre et al.

(10) Patent No.: US 8,008,090 B2
(45) Date of Patent: Aug. 30, 2011

(54) VAPOCHROMIC COORDINATION POLYMERS FOR USE IN ANALYTE DETECTION

(75) Inventors: Julie Lefebvre, Burnaby (CA); Michael Iacov Katz, North Vancouver (CA); Daniel B. Leznoff, Vancouver (CA)

(73) Assignee: Simon Fraser University, Burnaby (CA)

(*) Notice: Subject to any disclaimer, the term of this patent is extended or adjusted under 35 U.S.C. 154(b) by 298 days.

(21) Appl. No.: 11/577,299

(22) PCT Filed: Oct. 17, 2005

(86) PCT No.: PCT/CA2005/001601
§ 371 (c)(1),
(2), (4) Date: Nov. 28, 2007

(87) PCT Pub. No.: WO2006/039817
PCT Pub. Date: Apr. 20, 2006

(65) Prior Publication Data
US 2008/0071053 A1    Mar. 20, 2008

Related U.S. Application Data

(60) Provisional application No. 60/618,573, filed on Oct. 15, 2004.

(51) Int. Cl.
*G01N 21/00* (2006.01)
(52) U.S. Cl. .............. 436/164; 436/2; 436/80; 436/81; 436/126; 436/166; 436/167; 436/181; 436/183; 252/408.1
(58) Field of Classification Search .................. None
See application file for complete search history.

(56) References Cited

U.S. PATENT DOCUMENTS
4,826,774 A    5/1989 Nagel
(Continued)

FOREIGN PATENT DOCUMENTS
EP    0277033 B1    4/1994
(Continued)

OTHER PUBLICATIONS

Stender, Matthias, et al. New Structural Features of Unsupported Chains of Metal Ions in Luminescent [(NH3)4Pt][Au(CN)2]2.1.5(H2O) and Related Salts, 2003, Inorgainc Chemistry, vol. 42(15), p. 4504-4506.*

(Continued)

*Primary Examiner* — Yelena G Gakh
*Assistant Examiner* — Robert Xu
(74) *Attorney, Agent, or Firm* — Oyen Wiggs Green & Mutala LLP

(57) ABSTRACT

This application relates to vaprochromic coordination polymers useful for analyte detection. The vapochromism may be observed by visible color changes, changes in luminescence, and/or spectroscopic changes in the infrared (IR) signature. One or more of the above chromatic changes may be relied upon to identify a specific analyte, such as a volatile organic compound or a gas. The chromatic changes may be reversible to allow for successive analysis of different analytes using the same polymer. The polymer has the general formula MW[M'X(Z)Y]N wherein M and M' are the same or different metals capable of forming a coordinate complex with the Z moiety; Z is selected from the group consisting of halides, pseudohalides, thiolates, alkoxides and amides; W is between 1-6; X and Y are between 1-9; and N is between 1-5. Optionally, an organic ligand may be bound to M. In alternative embodiments of the invention M may be a transition metal, such as Cu and Zn, M' may be a metal such as Au, Ag, Hg and Cu, and Z may be a pseuodohalide, such as CN, SCN, SeCN, TeCN, OCN, CNO and NNN. In one particular embodiment a new class of [Metal(CN)2]-based coordination polymers with vapochromic properties is described, such as Cu[Au(CN)2]2 and Zn[Au(CN)2]2 polymers.

13 Claims, 10 Drawing Sheets

The extended 1-D zig-zag chain structure of Cu[Au(CN)₂]₂(DMSO)₂ (1).
DMSO-methyl groups were removed for clarity.

U.S. PATENT DOCUMENTS 4,834,909 A     5/1989    Nagel
5,766,952 A     6/1998    Mann et al.

FOREIGN PATENT DOCUMENTS

ES           2151424 B1       7/2001
ES           2151424 BA      7/2001

OTHER PUBLICATIONS

N. Blom et al., Thallium Dicyanoaurate(I), Tl[AU(CN)2], and Cesium Dicyanoaurate(I), Cs[Au(CN)2], Acta Cryst., C40, 1984, 1767-1769.

Angeline Stier & Klaus-Jurgen Range, Dicyanometallate, VII[1] Preparation and Crystal Structure of Gendolinium-tris-dicyanoaurat (I), Gd [Au(CN)2]3.2,3H2O, Z. Naturforsch, 51b, 1996, 698-702.

J. Chomic et al., Thermal Properties of Complexes M(NH3)2[Ag(CN)2]2 (M(II)=Ni, Cu, Cd, Chem. Papers 47(3), 1993, 175-178.

Bernard F. Hoskins et al., Six Interpenetrating Quartz-Like Nets in the Structure of ZnAu2(CN)4, Angew Chem. Int. Ed. Engl., 34, No. 11, 1995, 1203-1204.

C. Bariain et al., Detection of volatile organic compound vapors by using a vapochromic material on a tapered optical filter, Applied Physics Letters, vol. 7, No. 15, Oct. 9, 2000, 2274-2276.

Enrique Colacio et al., Aurophilicity as a cofactor in crystal engineering. Dicyanoarate(I) anion as a building block in a novel Co(II)-AU(I) bimetallic assembly, ChemComm, 2002, 592-593.

Takayoshi Soma and Toshitake Iwamoto, A Three-Dimensional Warp-and-Woof Structure Interwoven by a Couple of Two-Dimensional Network Layers in the Crystal Structure of [trans-Cd(NH3)2{Ag(CN)2}2]n, Chemistry Letters, 1995, 271-272.

Christopher L. Exstrom et al., Inclusion of Organic Vapors by Crystalline, Solvatochromic [Pt(aryl isonitrile)4][Pd(CN)4] Compounds, Chem. Mater., 7, 1995, 15-17.

Charles A. Daws et al., "Vapochromic" Compounds as Environmental Sensors. 2. Synthesis and Near-Infrared and Infrared Spectroscopy Studies of [Pt(arylisocyanide)4][Pt(CN)4] upon Exposure to Volatile Organic Compound Vapors, Chem. Mater., 9, 1997, 363-368.

Christopher L. Exstrom et al., Infrared Spectroscopy Studies of Platinum Salts Containing Tetracyanoplatinate(II), Chem. Mater., 10, 1998, 942-945.

Yoshihito Kunugi et al., A Vapochromic Photodiode, Chem. Mater., 10, 1998, 1487-1489.

Wen Dong et al., 3D porous and 3D interpenetrating triple framework structures constructed by aurophilicity-coordination interplay in {Mn[Au(CN)2]2(H2O)2}n and {KFe[Au(CN)2]3}n, ChemComm, 2003, 2544-2545.

Zerihun Assefa et al., Photoluminescence Studies of Lanthanide Ion Complexes of Gold and Silver Dicyanides: A New Low-Dimensional Solid State Class for Nonradiative Excited-State Energy Transfer, Inorganic Chemistry, 33, 1994, 2187-2195.

Eduardo J. Fernandez et al., A Detailed Study of the Vapochromic Behavior of {Tl{Au(C6Cl5)2]}n, Inorganic Chemistry, 43, 2004, 3573-3581.

Zerihun Assefa and Howard H. Patterson, Photoluminescence Studies of Lanthanide Ion Complexes of Gold and Silver Dicyanides. 2. A New Low Dimensional Solid State Class for Nonradiative Excited State Energy Transfer, Inorganic Chemistry, 33, 1994, 6194-6200.

W. B. Feldtmann, Gold-Zinc-Cyanide, The Journal of the Chemical, Metallurgical and Mining Society of South Africa, Vol. XX Aug. 1919. No. 2, 13-14.

Carrie E. Buss and Kent R. Mann, Synthesis and Characterization of Pt(CN-p-(C2H5)C6H4)2(CN)2, a Crystalline Vapoluminescent Compound That Detects Vapor-Phase Aromatic Hydrocarbons, J. Am. Chem. Soc., vol. 124, No. 6, 2002, 1031-1039.

M. Adnan Mansour et al., Linear Chain Au(I) Dimer Compounds as Environmental Sensors: A Luminescent Switch for the Defection of Volatile Organic Compounds, J. Am. Chem. Soc., 120, 1998, 1329-1330.

Eduardo J. Fernandez et al., {Tl[Au(C6Cl5)2]}n: A Vapochromic Complex, J. Am. Chem. Soc., vol. 125, No. 8, 2003, 2022-2023.

Rochelle L. White-Morris et al., Remarkable Variations in the Luminescence of Frozen Solutions of [Au{C(NHMe)2}2] (PF6).0.5(Acetone), J. Am. Chem. Soc., vol. 124, No. 10, 2002, 2327-2336.

Laurance G. Beauvais et al., Cyano-Bridged Re6Q8 (Q=S, Se) Cluster-Cobalt(II) Framework Materials: Versatile Solid Chemical Sensors, J. Am. Chem. Soc., vol. 122, No. 12, 2000, 2763-2772.

Carrie E. Buss et al., Structural Investigations of Vapochromic Behavior. X-ray Single-Crystal and Powder Diffraction Studies of [Pt(CN-iso-C3H7)4][M(CN)4] for M=Pt or Pd, J. Am. Chem. Soc., vol. 120, No. 31, 1998, 7783-7790.

Steven M. Drew et al., An Electronic Nose Transducer Array of Vapoluminescent Platinum(II) Double Salts, J. Am. Chem. Soc., vol. 123, No. 39, 2001, 8414-8415.

Manal A. Rawashdeh-Omary et al., Chemistry and Optoelectronic Properties of Stacked Supramolecular Entities of Trinuclear Gold(I) Complexes Sandwiching Small Organic Acids, J. Am. Chem. Soc., vol. 123, No. 39, 2001, 9689-9691.

S.C. Abrahams et al., Piezoelectric KCo[Au(CN)2]3: Room temperature crystal structure of a cobalt-hardened gold electrodeposition process component, J. Chem. Phys., 73(9), 1980, 4585-4590.

S.C. Abrahams et al., Cobalt cyanoaurate: Crystal structure of a component from cobalt-hardened gold electroplating baths, J. Chem. Phys., 76(11), 1982, 5458-5462.

Daniel B. Leznoff et al., An aurophilicity-determined 3-D bimetallic coordination polymer: using [Au(CN)2]− to increase structural dimensionality through gold . . . gold bonds in (tmeda)Cu[Au(CN)2]2, ChemComm, 2001, 259-260.

Daniel B. Leznoff et al., Gold-Gold Interactions as Crystal Engineering Design Elements in Heterobimetallic Coordination Polymers, Inorganic Chemistry, vol. 40, No. 23, 2001, 6026-6034.

Yoshihito Kunugi et al., AYoshihito Kunugi et al., A Vapochromic LED, J. Am. Chem. Soc., vol. 120, No. 3, 1998, 589-590 Vapochromic LED, J. Am. Chem. Soc., vol. 120, No. 3, 1998, 589-590.

Zerihun Assefa et al., Europium (III) Tris [dicyanoargentate (I)] Trihydrate, Eu [Ag (CN) 2] 3.3 H2O, Acta Cryst., C51, 1995, 2527-2529.

Wei Han et al., Synthesis and Characterisation of Two Supramolecular Polymers [CuAg4 (CN) 6 (tacn)] n and [CuAu2 (CN) 4 (tacn)] n Containing Metal-Metal Interactions, European Journal of Inorganic Chemistry, 10, 2004, 2130-2136.

\* cited by examiner

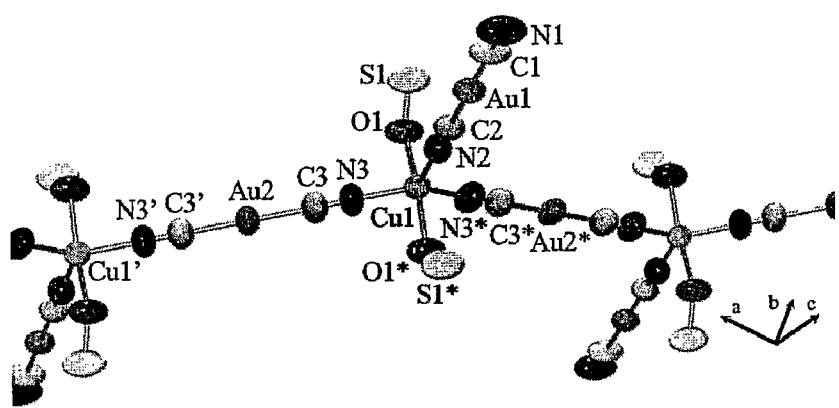
Figure 1. The extended 1-D zig-zag chain structure of Cu[Au(CN)$_2$]$_2$(DMSO)$_2$ (1). DMSO-methyl groups were removed for clarity.

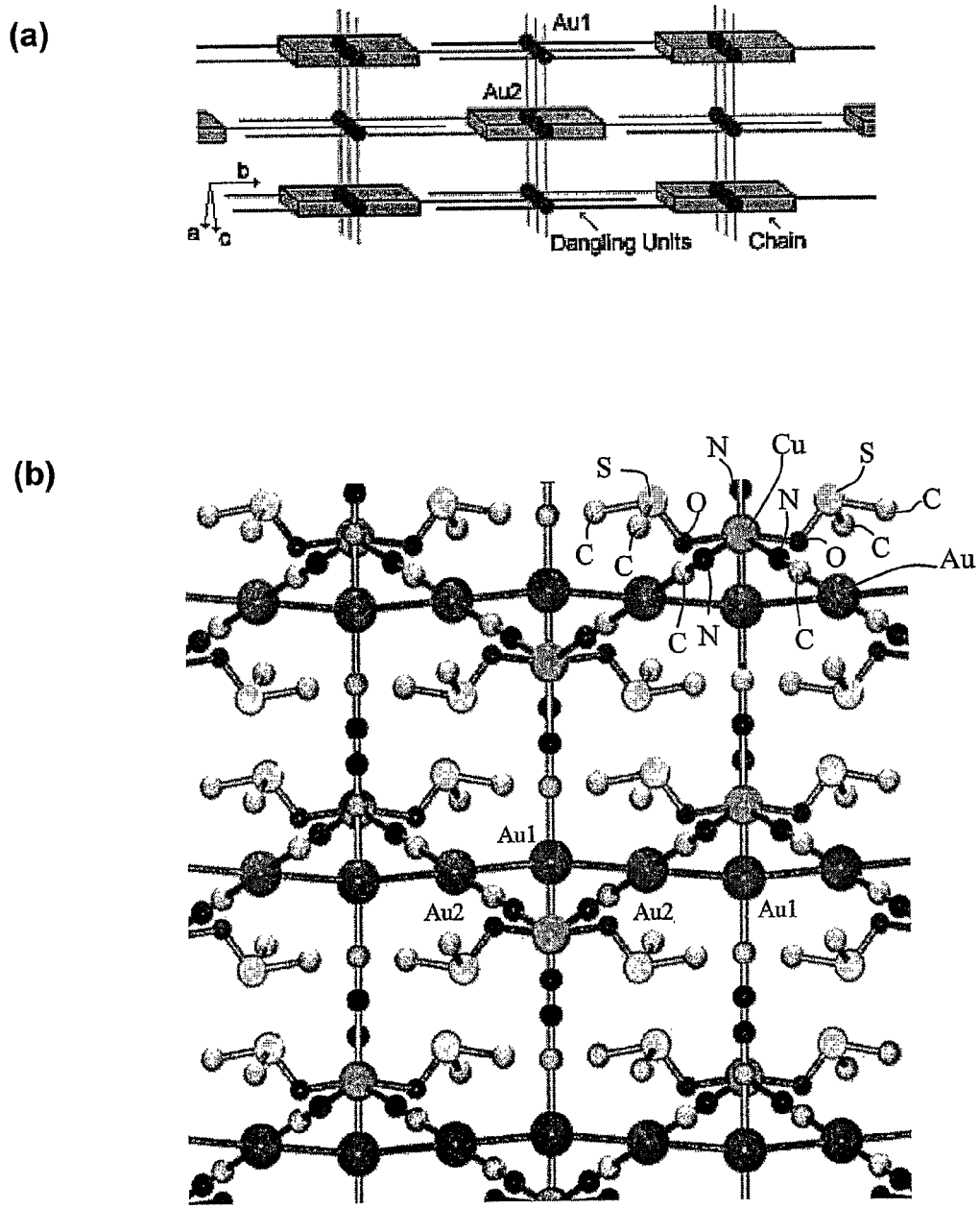
Figure 2. (a): Offset stacks of chains in 1, viewed down the (101)-plane (slightly tilted). Au-Au bonds connect bridging and dangling [Au(CN)$_2$]⁻ units of neighboring chains (vertical lines). (b): 3-D structure of 1 formed via Au-Au bonding, viewed down the $a$-axis.

(a)
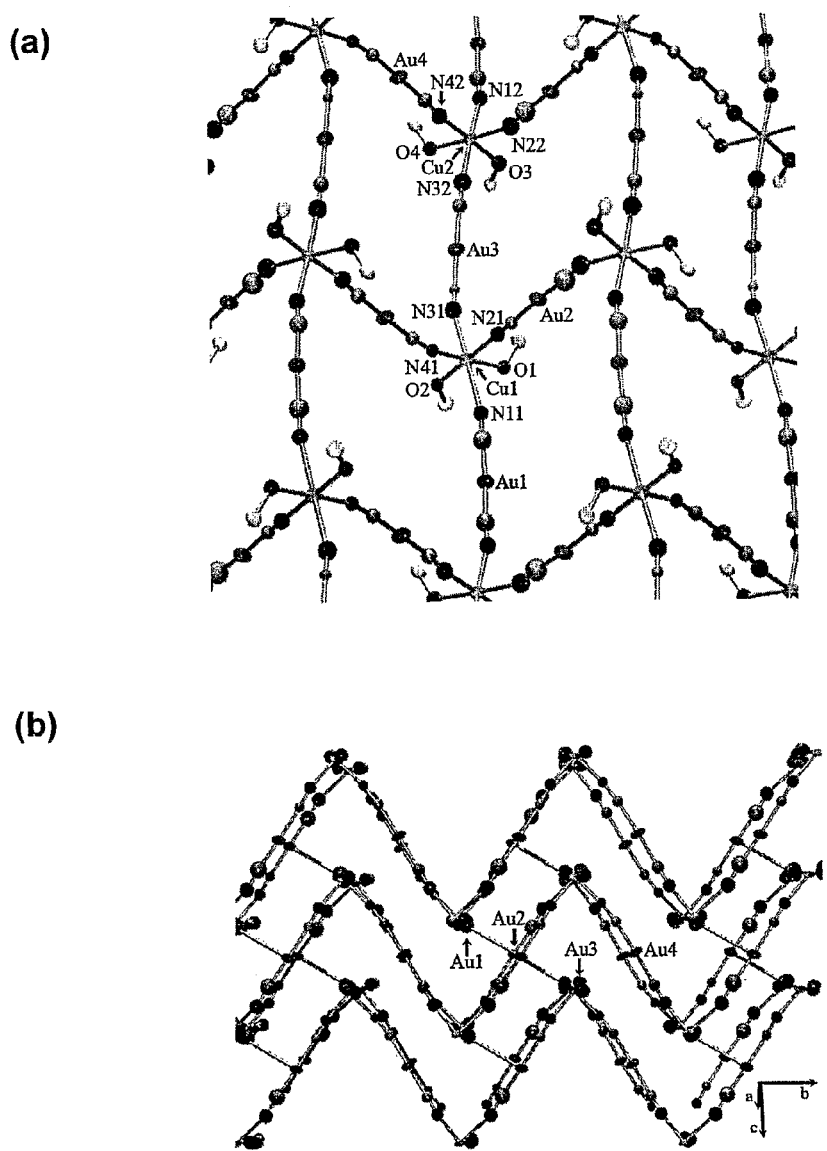
(b)
Figure 3. (a): Extended structure of 2 showing the 2-D corrugated layers, viewed down the *a*-axis. DMSO-methyl groups were removed for clarity. (b): Layers stacked via aurophilic interactions to yield a 3-D network.

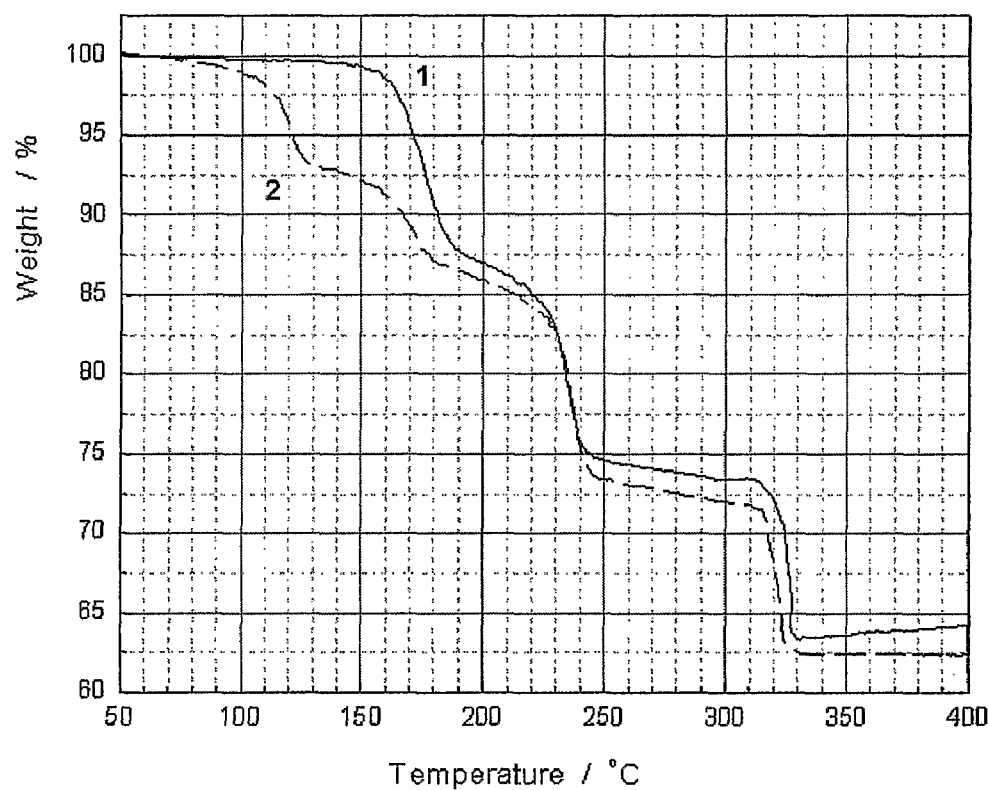
Figure 4. Thermal decomposition of polymorphs 1 and 2.

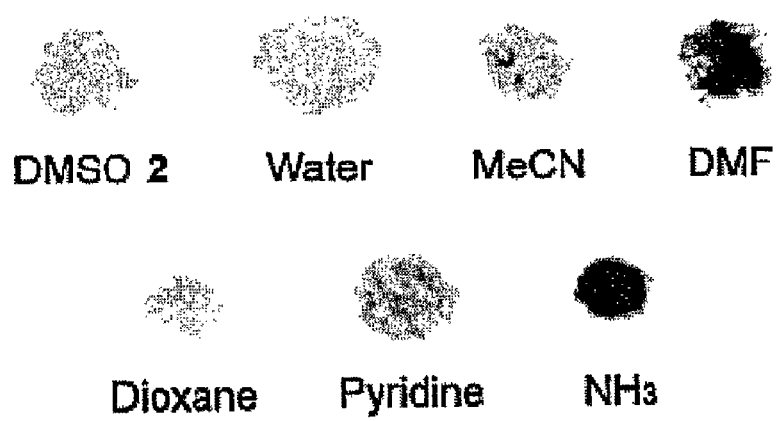
Figure 5. Powder sample of 2 exposed to various solvent vapours.

(a)
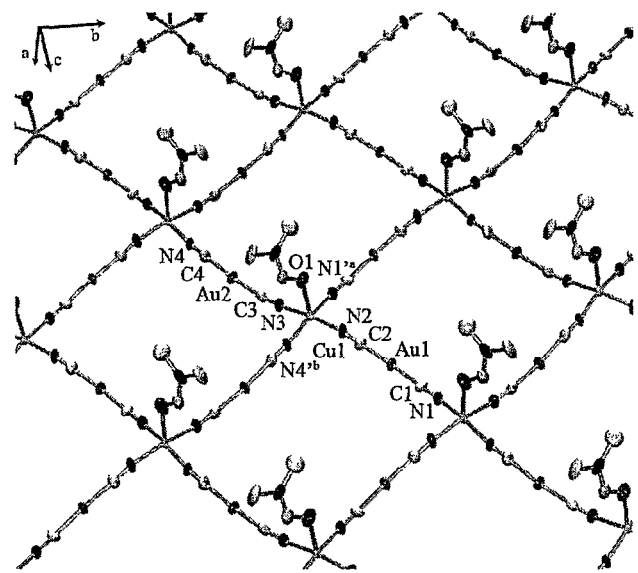
(b)
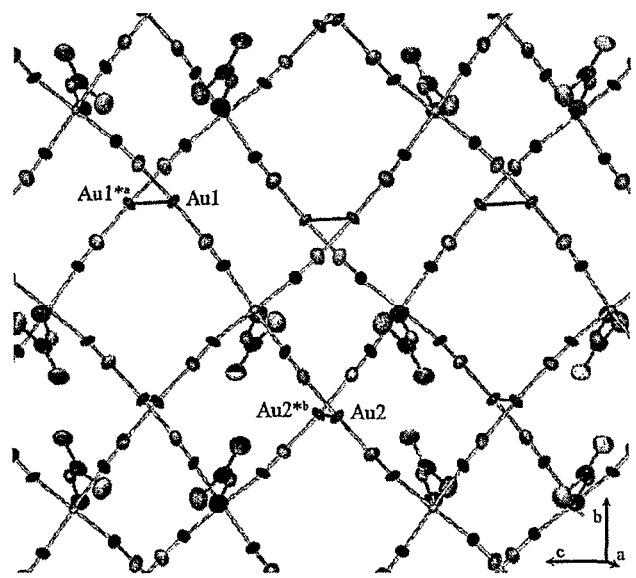
Figure 6. (a): Extended structure of 3 showing the 2-D layers (hydrogen atoms were removed for clarity). (b): Aurophilic interactions between the layers yield a 3-D network.

(a)
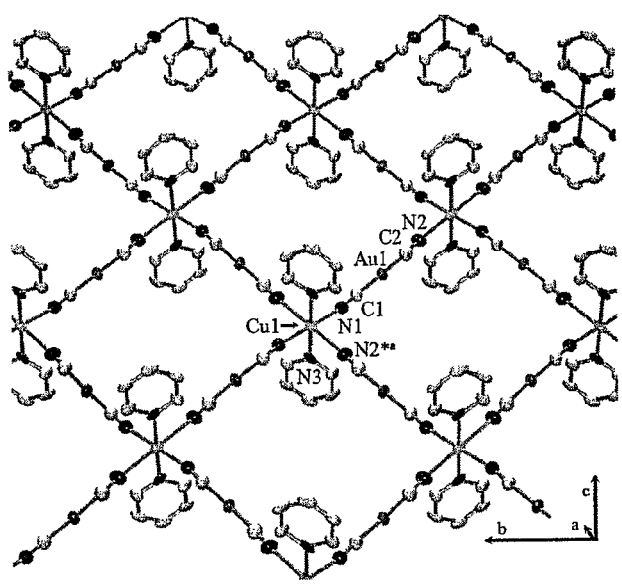
(b)
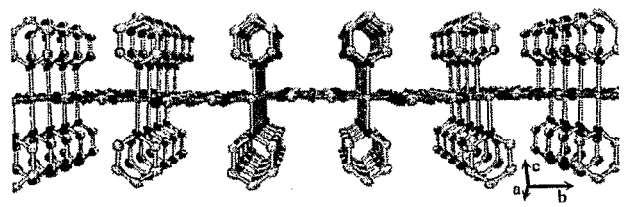
Figure 7. (a): Extended structure of 4 showing a 2-D layer. (b): Side view of a 2-D layer showing the pyridine ligands situated above and below the plane.

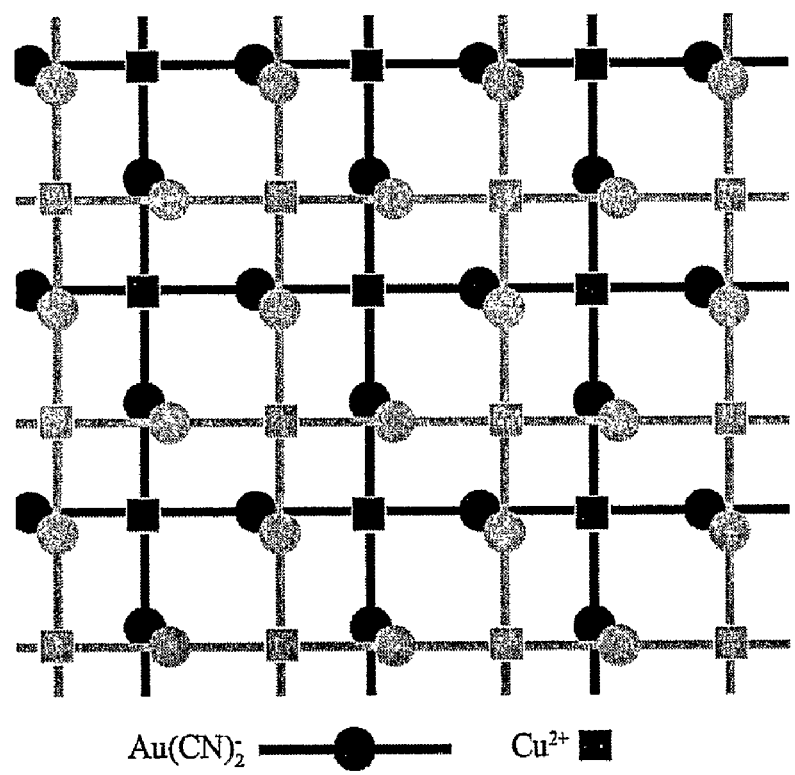
Figure 8. Postulated 2-D square grid structure of $Cu[Au(CN)_2]_2$.

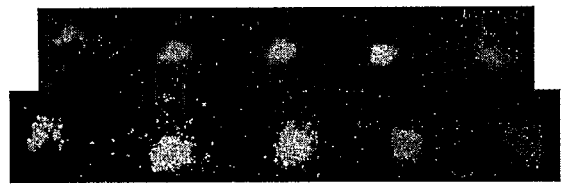
Figure 9. Changes in luminescence in the $Zn[Au(CN)_2]_2(analyte)_x$ system (top - under room light; bottom - under UV light). From left to right: Analyte = None, $NH_3$, pyridine, $CO_2$, DMSO. The cyanide-IR changes are dramatic and distinctive for each analyte.

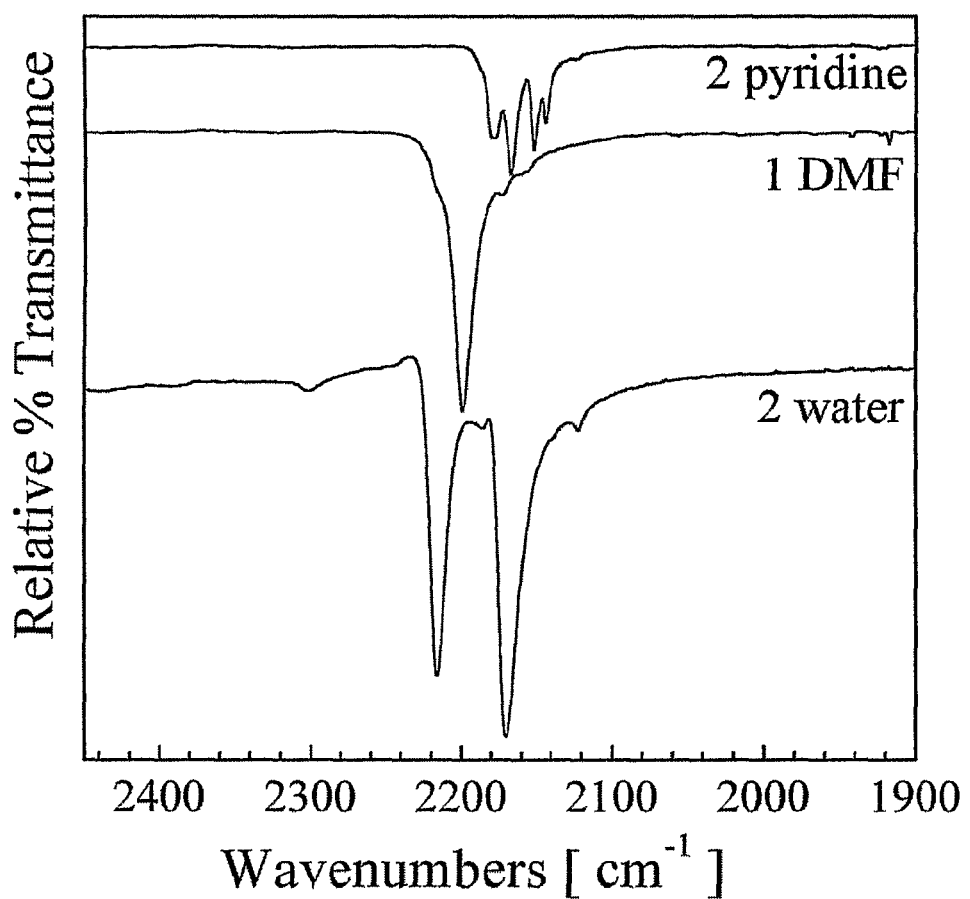
Figure 10. Spectrograph showing the comparative IR spectra in the cyanide region for the three analytes: pyridine, DMF and water.

VAPOCHROMIC COORDINATION POLYMERS FOR USE IN ANALYTE DETECTION

REFERENCE TO RELATED APPLICATIONS

This application claims the benefit of U.S. provisional patent application Ser. No. 60/618,573 filed 15 Oct. 2004 which is hereby incorporated by reference.

FIELD OF THE INVENTION

This application relates to coordination polymers having vapochromic properties useful for analyte detection.

BACKGROUND OF THE INVENTION

The controlled design and synthesis of metal-organic coordination polymers from the self-assembly of simple molecular building blocks is of intense interest due to the promise of generating functional materials.[1,2] Vapochromic materials, which display optical absorption or luminescence changes upon exposure to vapors of analytes, such as volatile organic compounds (VOCs), have been a focus of attention due to their potential applications as chemical sensors.[9-15] For example, when exposed to certain organic solvents, the extended Prussian Blue $Co^{2+}$—$[Re_6Q_8(CN)_6]^{4-}$ (Q=S, Se) system yields dramatic changes in the visible spectrum that are attributable to the sensed solvent impacting the geometry and hydration around the $Co^{II}$ centers.[15]

Several vapochromic compounds based on $Au^I$, $Pd^{II}$, and $Pt^{II}$ coordination polymers have also been reported.[9-14] The vapochromism in these systems is based on changes in both the visible absorption and emission spectra. In the linear $\{Tl[Au(C_6Cl_5)_2]\}_n$ polymer, weak interactions between the Tl atoms and the adsorbed VOC molecules modify slightly the color, and more significantly the emission spectra.[12] On the other hand, changes in the emission spectra of $[Pt(CN—R)_4][M(CN)_4]$ (R=iso-$C_3H_7$ or $C_6H_4$—$C_6H_4$—$C_nH_{2n+1}$; n=6, 10, 12, 14 and M=Pt, Pd) occur when metal-metal distances are modified due to the presence of VOC molecules in lattice voids; small changes in the absorption spectrum can also be observed.[13,16] Another example is the trinuclear $Au^I$ complex with carbeniate bridging ligands, for which its luminescence is quenched in the solid-state when $C_6F_6$ vapor is adsorbed due to the disruption of Au—Au interactions.[11]

Some of these vapochromic materials have recently been incorporated in chemical sensor devices. For example, [Au—$(PPh_2C(CSSAuC_6F_5)PPh_2Me)_2][ClO_4]$ has been used in the development of an optical fiber volatile organic compound sensor.[17] A vapochromic light emitting diode[18] and a vapochromic photodiode[19] have also been built using tetrakis(p-dodecylphenylisocyano) platinum tetranitroplatinate and bis (cyanide)-bis(p-dodecylphenylisocyanide)platinum(II), respectively.

In these previous discoveries, slight shifts in the $v_{CN}$ stretch are observed if hydrogen-bonding between the N(cyano) atoms and the VOC molecules present in the lattice occurs. Importantly, VOCs cannot be readily differentiated or identified via IR spectroscopy in this case since $v_{CN}$ shifts of only 0-10 cm$^{-1}$ are usually observed.[17,54,55]

To overcome the shortcomings of the prior art, the need has arisen for coordination polymers having improved vapochromic properties for enhancing the sensitivity of analyte detection. The IR signatures achieved by the present invention are unusually diagnostic for a particular analyte, both in the number and position of the IR bands. In the case of some gases, the adsorption of the analyte to the polymer substantially enhances the IR response. That is, the response in the $v_{CN}$ or other pertinent region of the spectrum is extremely strong compared to the direct IR-signature of some gases, which is the current state-of-the-art in gas sensors. Moreover, in the present invention the vapochromism of polymers can be readily and reversibly observed by multiple means, such as visible colour changes and luminescence changes in addition to IR spectroscopic changes.

SUMMARY OF THE INVENTION

In accordance with the invention, a vapochromic polymer is described having the general formula $M_W[M'_X(Z)_Y]_N$ wherein M and M' are the same or different metals capable of forming a coordinate complex with the Z moiety; Z is selected from the group consisting of halides, pseudohalides, thiolates, alkoxides and amides; W is between 1-6; X and Y are between 1-9; and N is between 1-5. For example, in one embodiment W and X are 1 and Y and N are 2.

The vapochromic properties of the polymer change when the polymer is exposed to different analytes. The polymer may therefore be used for analyte detection. The vapochromism may be observed by visible color changes, changes in luminescence, and/or spectroscopic changes in the infrared IR signature. One or more of the above chromatic changes may be relied upon to identify a specific analyte, such as a volatile organic compound or a gas. The chromatic changes may be reversible to allow for successive analysis of different analytes using the same polymer.

In alternative embodiments of the invention M may be a transition metal, such as Cu and Zn, M' may be a metal such as Au, Ag, Hg and Cu, and Z may be a pseuodohalide, such as CN, SCN, SeCN, TeCN, OCN, CNO and NNN. Optionally, an organic ligand may be bound to M. In one particular embodiment a new class of [Metal(CN)$_2$]-based coordination polymers with vapochromic properties is described, such as Cu[Au(CN)$_2$]$_2$ and Zn[Au(CN)$_2$]$_2$ polymers.

BRIEF DESCRIPTION OF THE DRAWINGS

In drawings which describe embodiments of the invention but which should not be construed as restricting the spirit or scope of the invention in any way, FIG. 1 is a diagram of the 1-D crystal structure of a first polymorph of Cu[Au(CN)$_2$]$_2$(DMSO)$_2$. DMSO-methyl groups were removed for clarity.

FIGS. 2(a) and (b) are diagrams of the 3-D crystal structure of the first polymorph of Cu[Au(CN)$_2$]$_2$(DMSO)$_2$.

FIGS. 3(a) and (b) are diagrams of the 2-D and 3-D crystal structure of a second polymorph of Cu[Au(CN)$_2$]$_2$(DMSO)$_2$.

FIG. 4 is a graph showing the thermal stability of the first and second polymorphs of Cu[Au(CN)$_2$]$_2$(DMSO)$_2$.

FIG. 5 is a photograph showing the vapochromic behavior of the second polymorph of Cu[Au(CN)$_2$]$_2$(DMSO)$_2$ after exposure to various analytes, namely DMSO, water, MeCN, DMF, Dioxane, Pyridine and NH$_3$.

FIGS. 6(a) and (b) are diagrams of the 2-D and 3-D crystal structure of Cu[Au(CN)$_2$]$_2$(DMF).

FIGS. 7(a) and (b) are diagrams of the 2D crystal structure of Cu[Au(CN)$_2$]$_2$(pyridine)$_2$.

FIG. 8 is a diagram of the postulated 2-D crystal structure of a solvent free complex of Cu[Au(CN)$_2$]$_2$.

FIG. 9 are photographs showing changes in luminescence in the Zn[Au(CN)$_2$]$_2$(analyte)$_x$ system (top—under room light; bottom—under UV light). From left to right: Analyte=None, NH$_3$, pyridine, CO$_2$, DMSO.

FIG. 10 is a spectrograph showing the comparative IR spectra in the cyanide region for three analytes (solvents), namely pyridine, DMF and water using the Cu[Au(CN)$_2$]$_2$ (solvent)$_x$ polymer.

DETAILED DESCRIPTION OF THE INVENTION

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

This application relates to vapochromic polymers useful for detection of analytes. The polymers have the general formula $M_W[M'_X(Z)_Y]_N$ wherein M and M' are the same or different metals capable of forming a coordinate complex in conjunction with the Z moiety; Z is selected from the group consisting of halides, pseudohalides, thiolates, alkoxides and amides; W is between 1-6; X and Y are between 1-9; and N is between 1-5. As will be apparent to a person skilled in the art and as described herein, the vapochromic polymers of the invention may also comprise other constituents including ligands, counterbalancing ions and other metals. The invention encompasses polymers having the same empirical formula as set out above which exhibit vapochromic properties.

As described below, the vapochromism of the polymers may be observed, for example, by (1) visible changes, such as changes in colour or luminescence upon exposure to analytes, and by (2) infrared (IR) spectroscopic changes. The invention thus provides multiple detection means or "channels" to thereby achieve highly sensitive analyte detection. As used in this patent application the term "vapochromic" refers to a material that has a spectroscopic property change upon exposure to a gas or liquid analyte (e.g. a volatile organic compound) and the term vapochromism refers to such a spectroscopic property change. The spectroscopic property may include any wavelength of light including microwaves, infrared, visible colour and luminescence. As used in this patent application the process of "detecting chromatic changes" includes detecting a spectroscopic property change, including both visible and non-visible changes resulting from exposure to an analyte.

As exemplified by the Examples described below, in some embodiments of the invention M is a transition metal such as copper (Cu) or zinc (Zn) and M' is a metal such as gold (Au), silver (Ag), mercury (Hg) or copper. The Z moiety may be an ion or anionic ligand. Suitable Z moieties include pseudohalide ions such as CN—. As will be apparent to a person skilled in the art, other suitable pseudohaldides include SCN, SeCN, TeCN, OCN, CNO and NNN. In particular embodiments of the invention Cu[Au(CN)$_2$]$_2$ and Zn[Au(CN)$_2$]$_2$ polymers are described. The Cu[Au(CN)$_2$]$_2$ embodiment takes advantage of the unique chemical properties of gold (I) and copper (II) ions, such as attractive gold-gold interactions and luminescence for gold and a flexible coordination sphere for copper. The attractive interactions enable the formation of chemically stable, high-dimensionality materials and the gold-luminescence, cyanide-IR and copper(II) visible spectrum can all act as simultaneous sensory outputs. Similarly, with respect to the Zn[Au(CN)$_2$]$_2$ embodiment, distinctive luminescence and other photochromic qualities are exhibited.

In other embodiments of the invention the metal M may be a 1$^{st}$ row transition metal other than Cu or Zn, such as Sc, Ti, V, Cr, Mn, Fe, Co, or Ni, or some other transition-metal such as Zr, Nb or Ru. M may also be a lanthanide. Although the Mn (water)[40], Fe (with K-salt)[40], Co (none, with K-salt[56,57], and DMF[41]), Zn (none)[58] and a few lanthanides (Gd, Eu, Yb—all with no ligands)[52,59-61] complexes are known in the prior art (ligands shown in brackets), no sensor or vapochromic properties for such complexes have been previously described.

Optionally, an organic ligand may be bound to M. The ligand may be any ligand capable of capping the metal cation, and may include nitrogen, oxygen, sulfur or phosphorus donors.

Depending upon the resultant charge of the $M_W[M'_X(Z)_Y]_N$ structure, a charge-balancing ion, either a cation or anion, may also be present. For example, a charge balancing ion may be required where M' is Hg.

In alternative embodiments of the invention the metal M' may be selected to produce both linear metal cyanides or non-linear cyanides. For example, cyanometallate units such as [Au(CN)$_2$]$^-$, [Ag(CN)$_2$]$^-$ or [Hg(CN)$_2$] may be incorporated into polymers in conjunction with different transition metal cations and supporting ligands according to the following general equation:[31-33,63-68]

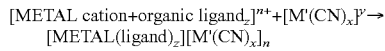

$$[\text{METAL cation+organic ligand}_z]^{n+} + [M'(CN)_x]^{y-} \rightarrow [\text{METAL}(\text{ligand})_z][M'(CN)_x]_n$$

(n=1-5, x=2-9, y=−5 to 0, z=0-9)

The synthesis may be readily accomplished in solvents such as water or alcohols. Compared to prior art approaches, the polymers and polymer-analyte compositions of the present invention can be prepared from extremely simple commercially available starting materials in minimal steps. As described in the Examples section below, the synthetic methodology, which has built-in design flexibility, low-cost and simple synthesis, is also a general advantage of coordination polymer systems over current zeolitic technology. The system is modular in that the metal cation and organic ligand can be chosen as desired to target a particular application or property.

An important advantage of embodiments of the invention described herein is that the vapochromic properties of the polymers may be reversible. For example, the Cu[Au(CN)$_2$]$_2$ embodiment shows reversible vapochromic sensor behaviour attributable to the Cu—Au pairing.[62] Starting with a solid of any Cu[Au(CN)$_2$]$_2$(solvent)$_x$, addition of a different solvent vapour (analytes) generates a new complex. As described below, exceptions may apply in the case of very strong donor solvents such as pyridine or ammonia, which bind strongly to the Cu$^{II}$ center and are not easily displaced by other solvents. Similarly, the Zn[Au(CN)$_2$]$_2$ embodiment exhibits reversible vapoluminescent material qualities.[69] The polymers of the invention may thus be employed in a dynamic system for successively detecting different analytes without the need for reinitialization (although reinitialization may still be required to repeatedly detect the same analyte).

The invention may be used for detecting a wide variety of analytes including volatile organic compounds (VOCs) and gases. The solid polymers adsorb (i.e. bind or trap) analyte, such as organic solvents, exposed to the polymers in a vapour (or liquid) phase. The detectable VOCs typically include a hetero (non-carbon) atom donor such as hydrogen, nitrogen, oxygen, sulfur and phosphorus donors. Examples of solvent vapours that will effectively adsorb to the polymers of the invention include pyridine, dioxane, water, ethanethiol and trimethylphosphine. Donor gases such as H$_2$S and ammonia also readily bind and are detectable. The binding capacity and sensitivity of the polymers may be adjusted through altering the identity of the metals M and M' to enable detection of a range of gases, including but not limited to NO$_x$, SO$_x$, CO$_x$ and allenes. For example, the zinc-based polymer described herein appears to bind CO and $CO_2$ and may have applications as a CO or $CO_2$-sensor.

As will be appreciated by a person skilled in the art, the polymers of the invention may find application in wide range of industrial and commercial applications, such as in the chemical, energy and environmental sectors. The polymers may be used in many different solid forms depending upon the vapochromic application, such as powders, crystals, thin films or combinations thereof. Exemplary industrial applications include: personal and badge monitors in chemical laboratories (e.g. industrial chemical or pharmaceutical research laboratories, paint and coatings manufacturing, cosmetics manufacturing) for hazardous vapour detection; portable or stationary threshold monitors for chemical vapours in laboratory environments or chemical storage facilities for hazardous vapour detection or regulated emission requirements; environmental sensor for volatile organic compounds or gases ("electronic noses") for use at environmental remediation sites, landfills, air-quality monitoring etc.; and responsive coatings, art supplies, colour-changing paint and other related applications where a colour-changing material is desired.

Although the present invention has been principally described in relation to analyte sensing and detection, the polymers and compositions described herein may be useful for other purposes such as extraction, purification and storage applications.

EXAMPLES

The following examples will further illustrate the invention in greater detail although it will be appreciated that the invention is not limited to the specific examples.

The following description of experimental details and experimental results is presented in multiple parts. Example 1.0 describes synthetic procedures and experimental results for the $Cu[Au(CN)_2]_2(solvent)_x$ system. Example 2.0 briefly describes a similar synthetic procedure and experimental results for an analogous $Zn[Au(CN)_2]_2(solvent)_x$ system.

Example 1.0

1.1 $Cu[Au(CN)_2]_2(solvent)_x$ System 1.1.1 Experimental Apparatus and General Procedure General Procedure and Physical Measurements. All manipulations were performed in air. All the reagents were obtained from commercial sources and used as received. Infrared spectra were recorded as KBr pressed pellets on a Thermo Nicolet Nexus 670 FT-IR spectrometer. Microanalyses (C, H, N) were performed at Simon Fraser University. Magnetic susceptibilities were measured on polycrystalline samples at 1 T between 2 and 300 K using a Quantum Design MPMS-5S SQUID magnetometer. All data were corrected for temperature independent paramagnetism (TIP), the diamagnetism of the sample holder, and the constituent atoms (by use of Pascal constants).[20] Solid-state UV-visible reflectance spectra were measured using an Ocean Optics SD2000 spectrophotometer equipped with a tungsten halogen lamp. Thermogravimetric analysis (TGA) data were collected using a Shimadzu TGA-50 instrument in an air atmosphere.

Synthesis of $Cu[Au(CN)_2]_2(DMSO)_2$, 1: A 0.5 mL dimethylsulfoxide (DMSO) solution of $Cu(ClO_4)_2.6H_2O$ (0.037 g, 0.1 mmol) was added to a 0.5 mL DMSO solution of $KAu(CN)_2$ (0.057 g, 0.2 mmol). Green crystals of $Cu[Au(CN)_2]_2(DMSO)_2$ were obtained by slow evaporation over several days, filtered and air-dried. Yield: 0.050 g, 70%. Anal. Calcd. for $C_8H_{12}N_4Au_2CuO_2S_2$: C, 13.39; H, 1.69; N, 7.81. Found: C, 13.43; H, 1.72; N, 7.61. IR (KBr): 3005(w), 2915 (w), 2184(s), 2151(m), 1630(w), 1426(w), 1408(w), 1321 (w), 1031(m), 993(s), 967(m), 720(w), 473(m) $cm^{-1}$. The same product can be obtained by absorption of DMSO by $Cu[Au(CN)_2]_2(H_2O)_2$.

Synthesis of $Cu[Au(CN)_2]_2(DMSO)_2$, 2: A 0.2 mL DMSO solution of $Cu(ClO_4)_2.6H_2O$ (0.037 g, 0.1 mmol) was added to a 0.4 mL DMSO solution of $KAu(CN)_2$ (0.057 g, 0.2 mmol). Blue needles of $Cu[Au(CN)_2]_2(DMSO)_2$ formed after one hour and were filtered and dried under $N_2$. Yield: 0.057 g, 80%. Anal. Calcd. for $C_8H_{12}N_4Au_2CuO_2S_2$: C, 13.39; H, 1.69; N, 7.81. Found: C, 13.50; H, 1.76; N, 7.62. IR (KBr): 3010(w), 2918(w), 2206(m), 2194(s), 2176(m), 2162 (m), 1631(w), 1407(w), 1316(w), 1299(w), 1022(m), 991(s), 953(m), 716(w), 458(m) $cm^{-1}$.

Synthesis of $Cu[Au(CN)_2]_2(DMF)$, 3: A 2 mL N,N-dimethylformamide (DMF) solution of $Cu(ClO_4)_2.6H_2O$ (0.037 g, 0.1 mmol) was prepared. This solution was added to a 3 mL DMF solution of $KAu(CN)_2$ (0.057 g, 0.2 mmol). A dark blue-green mixture of powder and crystals of $Cu[Au(CN)_2]_2$ (DMF) was obtained after several days of slow evaporation and was filtered and air-dried. Yield: 0.033 g, 52%. Anal. Calcd for $C_7H_7N_5Au_2CuO$: C, 13.25; H, 1.11; N, 11.04. Found: C, 13.26; H, 1.11; N, 11.30. IR (KBr): 2927(w), 2871(w), 2199(s), 2171(shoulder), 1665(s), 1660(s), 1492 (w), 1434(w), 1414(w), 1384(m), 1251(w), 1105(w), 674(w), 516(w), 408(w) $cm^{-1}$. Single crystals of 3 were obtained by dissolving $Cu[Au(CN)_2]_2(H_2O)_2$ (5) in DMF and allowing the solution to evaporate very slowly. The single crystals and the crystal/powder mixture as prepared above had identical IR spectra. The same product can also be obtained by vapour absorption of DMF by several $Cu[Au(CN)_2]_2(solvent)_x$ complexes.

Synthesis of $Cu[Au(CN)_2]_2(pyridine)_2$, 4: A 10 mL pyridine/water/methanol (5:47.5:47.5) solution of $Cu(ClO_4)_2.6H_2O$ (0.111 g, 0.3 mmol) was prepared. This solution was added to a 10 mL pyridine/water/methanol (5:47.5:47.5) solution of $KAu(CN)_2$ (0.171 g, 0.59 mmol). A blue powder of $Cu[Au(CN)_2]_2(pyridine)_2$ was obtained immediately and was filtered and air-dried. Yield: 0.163 g, 75%. Anal. Calcd for $C_{14}H_{10}N_6Au_2Cu$: C, 23.36; H, 1.40; N, 11.68. Found: C, 23.52; H, 1.44; N, 11.58. IR (KBr): 3116(w), 3080(w), 2179(s), 2167(s), 2152(s), 2144(m), 1607(m), 1449(m), 1445(s), 1214(m), 1160(w), 1071(m), 1044(w), 1019(m), 758(s), 690(s), 642(m) $cm^{-1}$. Single crystals of 4 were obtained by slow evaporation of the remaining solution. The crystals and powder had identical IR spectra. The same product can also be obtained by vapour absorption of pyridine by several $Cu[Au(CN)_2]_2(solvent)_x$ complexes.

Synthesis of $Cu[Au(CN)_2]_2(H_2O)_2$, 5: A 10 mL aqueous solution of $Cu(ClO_4)_2.6H_2O$ (0.259 g, 0.7 mmol) was prepared and added to a 10 mL aqueous solution of $KAu(CN)_2$ (0.403 g, 1.4 mmol). A pale green powder of $Cu[Au(CN)_2]_2$ $(H_2O)_2$ formed immediately and was filtered and air-dried. Yield: 0.380 g, 91%. The same product can be obtained by vapour absorption of water by several $Cu[Au(CN)_2]_2$(solvent)$_x$ complexes. Anal. Calcd for $C_4H_4N_4Au_2CuO_2$: C, 8.04, H, 0.67, N, 9.38. Found: C, 8.18; H, 0.71; N, 9.22. IR (KBr): 3246(m), 2217(s), 2194(vw), 2171(s), 1633(w) $cm^{-1}$.

Synthesis of $Cu[Au(CN)_2]_2$, 6: $Cu[Au(CN)_2]_2(H_2O)_2$ was heated (150° C.) in vacuo to yield green-brown $Cu[Au(CN)_2]_2$. The yield is quantitative, with no $v_{CN}$ peaks for hydrated 5 observable. Anal. Calcd for $C_4N_4Au_2Cu$: C, 8.56, H O, N, 9.98. Found: C, 8.68, H trace, N, 9.80. IR (KBr): 2191(s), 1613(vw), 530(m) $cm^{-1}$.

Synthesis of Cu[Au(CN)$_2$]$_2$(CH$_3$CN)$_2$, 7: A 1 mL CH$_3$CN solution of Cu(ClO$_4$)$_2$·6H$_2$O (0.037 g, 0.1 mmol) was prepared and added to a 2 mL CH$_3$CN solution of KAu(CN)$_2$ (0.057 g, 0.2 mmol). A green powder of Cu[Au(CN)$_2$]$_2$(CH$_3$CN)$_2$ precipitated immediately along with a white powder of KClO$_4$. To prevent the replacement of CH$_3$CN by atmospheric water, the solvent was removed under vacuum and the KClO$_4$ side product was not removed through washing and filtering. Anal. Calcd for Cu[Au(CN)$_2$]$_2$(CH$_3$CN)$_2$+ 2(KClO$_4$) (C$_8$H$_6$N$_6$Au$_2$Cl$_2$CuK$_2$O$_8$): C, 10.44; H, 0.65; N, 9.12. Found: C, 10.99; H, 0.57; N, 8.69. IR (KBr): 2297(w), 2269(w), 2192(s), 1600(w), 1445(w), 1369(w), 1088(s), 941 (w), 925(w), 752(w), 695(w), 626(m), 512(w), 468(w), 419 (w) cm$^{-1}$. The same product (without KClO$_4$) can be obtained by vapour absorption of acetonitrile by Cu[Au(CN)$_2$]$_2$(DMSO)$_2$ (1 or 2).

Synthesis of Cu[Au(CN)$_2$]$_2$(dioxane)(H$_2$O), 8: A 2 mL dioxane/water (2:1) solution of Cu(ClO$_4$)$_2$·6H$_2$O (0.037 g, 0.1 mmol) was prepared. This solution was added to a 4 mL dioxane/water (2:1) solution of KAu(CN)$_2$ (0.057 g, 0.2 mmol). A pale blue-green powder of Cu[Au(CN)$_2$]$_2$(dioxane)(H$_2$O) was obtained immediately and was filtered and air-dried. Yield: 0.057 g, 85%. The same product can be obtained by vapour absorption of dioxane by several Cu[Au(CN)$_2$]$_2$(solvent)$_x$ complexes (the water molecule included in this case is from ambient moisture). Anal. Calcd for C$_8$H$_{10}$N$_4$Au$_2$CuO$_3$: C, 14.39; H, 1.51; N, 8.39. Found: C, 14.31; H, 1.21; N, 8.43. IR (KBr): 2976(m), 2917(m), 2890 (w), 2862(m), 2752(w), 2695(w), 2201(s), 2172(w), 1451 (m), 1367(m), 1293(w), 1255(s), 1115(s), 1081(s), 1043(m), 949(w), 892(m), 871(s), 705(w), 610(m), 515(m), 428(m) cm$^{-1}$.

Synthesis of Cu[Au(CN)$_2$]$_2$(NH$_3$)$_4$, 9: This product was obtained by vapour absorption of NH$_3$ by several Cu[Au(CN)$_2$]$_2$(solvent)$_x$ complexes. The yield is quantitative as shown by IR. Anal. Calcd for C$_4$H$_{12}$N$_8$Au$_2$Cu: C, 7.63, H, 1.92, N, 17.80. found: C, 7.56; H, 1.98; N, 17.71. IR (KBr): 3359(s), 3328(s), 3271(s), 3212(m), 3182(m), 2175(m), 2148(s), 1639(m), 1606(m), 1243(s), 685(s), 435(w) cm$^{-1}$.

X-Ray Crystallographic Analysis. Cu[Au(CN)$_2$]$_2$(DMSO)$_2$ 1 and 2, Cu[Au(CN)$_2$]$_2$(DMF) 3 and Cu[Au(CN)$_2$]$_2$(pyridine)$_2$ 4: Crystallographic data for all structures are collected in Table 1. Crystals 1, 3 and 4 were mounted on glass fibers using epoxy adhesive and crystal 2 was sealed in a glass capillary. Crystal 1 was a green rectangular plate (0.09×0.12×0.3 mm$^3$), crystal 2 was a pale blue needle (0.11× 0.11×0.2 mm$^3$), crystal 3 was a green needle (0.09×0.09×0.15 mm$^3$) and crystal 4 was a dark blue platelet (0.02×0.06×0.15 mm$^3$).

For 1, data in the range 4°<2θ<55° were recorded using the diffractometer control program DIFRAC[21] and an Enraf Nonius CAD4F diffractometer. The NRCVAX Crystal Structure System was used to perform psi-scan absorption correction (transmission range: 0.0301-0.1726) and data reduction, including Lorentz and polarization corrections.[22] All non-hydrogen atoms were refined anisotropically. Full matrix least-squares refinement (1231 reflections included) on F (93 parameters) converged to $R_1$=0.042, $wR_2$=0.047 ($I_o$>2.5σ ($I_o$)).

For 2, 3 and 4, data in the ranges 6.9°<2θ<136.1°, 9.2°<2θ<144.0° and 12.0°<2θ<142.6° respectively were recorded on a Rigaku RAXIS RAPID imaging plate area detector. A numerical absorption correction was applied (transmission range: 0.019-0.161, 0.0070-0.0199 and 0.3484-0.5826) and the data were corrected for Lorentz and polarization effects.[23] For 2, the Au, Cu and S atoms were refined anisotropically, while the remainders were refined isotropically. For 3 and 4, all non-hydrogen atoms were refined anisotropically. Full matrix least-squares refinement on F was performed on 2, 3 and 4, the data converging to the following results: for 2, $R_1$=0.062, $wR_2$=0.082 ($I_o$>3.0σ($I_o$), 2026 reflections included, 205 parameters); for 3, $R_1$=0.0315, $wR_2$=0.0456 ($I_o$>3.0σ($I_o$), 1538 reflections included, 148 parameters); for 4, $R_1$=0.0276, $wR_2$=0.0401 ($I_o$>3.0σ($I_o$), 1021 reflections included, 107 parameters).

All structures were refined using CRYSTALS.[24] The structures were solved using Sir 92 and expanded using Fourier techniques. Hydrogen atoms were included geometrically in all structures but not refined. Diagrams were made using Ortep-3 (version 1.076)[25] and POV-Ray (version 3.6.0)[26]. Selected bond length and angles for 1-4 are reported in Tables 2 to 5 respectively.

1.1.2 Results

Synthesis. The reaction of Cu$^{II}$ salts with KAu(CN)$_2$ in dimethylsulfoxide (DMSO) produced two different compounds, depending on the total concentration of starting reagents. In dilute solution, green crystals of polymorph 1 formed slowly, whereas blue crystals of polymorph 2 were obtained rapidly in a highly concentrated solution. The IR spectra of 1 and 2 show different features (Table 6); the higher-energy bands likely correspond to bridging CN-groups, while the lower-energy bands are due to either free or loosely bound CN-groups.[27] The X-ray crystal structures of 1 and 2 revealed two different polymeric networks, both with the same empirical formula Cu[Au(CN)$_2$]$_2$(DMSO)$_2$, as confirmed by elemental analysis.

Crystal Structure of the Green Cu[Au(CN)$_2$]$_2$(DMSO)$_2$ Polymorph, 1. The five-coordinate Cu$^{II}$ center in 1 has a τ-value[28] of 0.44, where τ=0 is pure square pyramidal and τ=1 is pure trigonal bipyramidal, suggesting that the coordination geometry could be considered equally distorted from either polyhedron. The Cu$^{II}$ center is bound to two DMSO-O atoms (O—Cu—O=167.06°) and three N(cyano) atoms (FIG. 1). Selected bond lengths and angles for 1 are listed in Table 2. The asymmetric unit contains two different [Au(CN)$_2$]$^-$ units: a CuI-bridging moiety that generates a 1-D chain, and a Cu$^{II}$-bound dangling group. The chains stack on top of each other parallel to the (101)-plane, forming stacks of chains that are offset to allow interdigitation of the dangling [Au(CN)$_2$]$^-$ units. Each chain is connected to the four neighbouring chains through Au—Au interactions of 3.22007(5) Å between the Au(1) atoms of each dangling group and the Au(2) atoms of the chain backbone (FIG. 2(a)). The DMSO molecules occupy the channels between the chains; these channels are delineated by both [Au(CN)$_2$] groups and Au—Au bonds (FIG. 2(b)). A viable Au—Au interaction is considered to exist when the distance between the two atoms is less than 3.6 Å, the sum of the van der Waals radii for gold.[29]

Crystal Structure of the Blue Cu[Au(CN)$_2$]$_2$(DMSO)$_2$ Polymorph, 2. The structure of polymorph 2 contains Cu$^{II}$ centers in a Jahn-Teller distorted octahedral geometry, with the two DMSO molecules bound in a cis-equatorial fashion (O—Cu—O=95.2°) rather than in the nearly 180°-arrangement in 1. Selected bond lengths and angles for 2 are found in Table 3. The four remaining sites (two axial and two equatorial) are occupied by N(cyano) atoms of bridging [Au(CN)$_2$]$^-$ units, generating corrugated 2-D sheets (FIG. 3(a)). These 2-D layers stack (FIG. 3(b)) and are held together by weak Au(1)-Au(2) interactions of 3.419(3) Å and perhaps weak Au(3) . . . Au(4) contacts of 3.592(4) Å. Thus, the colour difference between the two polymorphs can be attributed to the different coordination number and geometry around the $Cu^{II}$ centers. That said, the coarse features of 1, namely the rectangular "channels" filled with DMSO molecules, are also clearly delineated in 2.

Magnetic Properties. As polymorphs 1 and 2 clearly have significantly different solid-state structures, it follows that their physical and chemical properties may also vary; this is obviously the case for their solid-state optical reflectance spectra, which show $\lambda_{max}$ of 550±7 and 535±15 nm respectively (Table 6). To explore this key issue, a series of representative properties were investigated. For example, the magnetic susceptibilities of 1 and 2 were measured at temperatures varying from 300 to 2 K. At 300 K, $\mu_{eff}$=1.98 and 1.93$\mu_B$ for 1 and 2 respectively, typical for $Cu^{II}$ centers.[30] As the temperature drops, $\mu_{eff}$ decreases and reaches 1.74 and 1.67$\mu_B$ at 2 K for 1 and 2 respectively. There is no maximum in either $\chi_M$ vs T plot. This behaviour is consistent with weak antiferromagnetic coupling, probably mediated by the diamagnetic $Au^I$ center.[31-34] Thus, the two polymorphs have similar magnetic properties.

Thermal stability. Examining the thermal stabilities of 1 and 2 by thermogravimetric analysis (FIG. 4), 1 loses its first DMSO molecule from 150-190° C. and the other one from 210-250° C. For polymorph 2 (which has 4 crystallographically distinct DMSO molecules), the first two DMSO molecules are lost between 100-135° C. and then 150-190° C., while the two remaining DMSO molecules dissociate around 210-250° C., comparable with 1. Both polymorphs are then stable until 310° C., at which point cyanogen ($C_2N_2$) is released, consistent with the decomposition of the Cu[Au(CN)$_2$]$_2$ framework.[35] Hence, the thermal stabilities of the two polymorphs with respect to the loss of the first DMSO molecules are significantly different. Differential scanning calorimetry shows no evidence for the thermal interconversion in the solid state from 2 to 1 below the decomposition temperature of 2.

Vapochromic Behavior. Interestingly, even though both polymorphs are thermally stable up to at least 100° C., the DMSO molecules can easily be replaced by ambient water vapour at room temperature to yield Cu[Au(CN)$_2$]$_2$(H$_2$O)$_2$ (5), as shown by elemental and thermogravimetric analysis. Despite the fact that both polymorphs have different solid-state structures, IR spectroscopy and powder X-ray diffraction show that both polymorphs convert to the same Cu[Au(CN)$_2$]$_2$(H$_2$O)$_2$ (5) complex (Table 6). This conversion is reversible. However, if DMSO vapour is added back to 5, only the green polymorph Cu[Au(CN)$_2$]$_2$(DMSO)$_2$ (1) is formed, even if the original DMSO-complex to which H$_2$O was added was the blue polymorph (2). The exchange of DMSO for H$_2$O can be observed visually from the associated colour change (FIG. 5).

Cu[Au(CN)$_2$]$_2$(DMSO)$_2$ (either 1 or 2) also displays vapochromic behaviour when exposed to a variety of other donor solvent vapours (i.e. analytes) in addition to H$_2$O. Each Cu[Au(CN)$_2$]$_2$(solvent)$_x$ complex can be distinguished easily by its colour (FIG. 5 and Table 6). In addition, the $v_{CN}$ region of the IR spectrum for each solvent complex is a characteristic, sensitive signature for that solvent (Table 6). FIG. 10 is a spectrograph showing the comparative IR spectra in the cyanide region for three solvents (i.e. analytes), namely pyridine, DMF and water using the Cu[Au(CN)$_2$]$_2$(solvent)$_x$ polymer. FIG. 10 show graphically the characteristic, sensitive signature for each solvent in the $v_{CN}$ region of the IR spectrum. Thus both the visible colour changes and the cyanide-IR changes are dramatic and distinctive for each analyte, allowing for more specific and sensitive analyte detection.

Importantly, this solvent exchange is completely reversible, thus permitting dynamic solvent sensing. As indicated in the above synthetic examples, starting with a solid of Cu[Au(CN)$_2$]$_2$(solvent)$_x$, addition of a different solvent vapour generates a new complex. The only exceptions occur in the case of very strong donor solvents such as pyridine or ammonia, which bind strongly to the $Cu^{II}$ center and are not easily displaced by other solvents.

Each Cu[Au(CN)$_2$]$_2$(solvent)$_x$ complex was also synthesized by reacting Cu(II) salts with [Au(CN)$_2$]$^-$ in the appropriate solvent and each was found, by elemental analysis, IR spectroscopy, TGA, and crystallography, to be identical to the complex generated by solvent exchange. In every case, elemental analysis and TGA (Table 7) indicate that the number of solvent molecules incorporated into the complex per transition metal center is always the same as the number incorporated by vapour adsorption. This is easily rationalized by the fact that all adsorbed solvent molecules are ligated to the $Cu^{II}$ center in a 1:1, 1:2 or, in the case of ammonia, a 1:4 ratio, with no additional loosely trapped solvent molecules in channels (as shown by TGA, Table 7), as is often observed in other porous systems that include solvent.[36-39]

Crystal Structure of Cu[Au(CN)$_2$]$_2$(DMF), 3. In order to better understand the structural changes that occur during a vapochromic response of the DMSO polymorphs, the structures of Cu[Au(CN)$_2$]$_2$(DMF) (3) and Cu[Au(CN)$_2$]$_2$(pyridine)$_2$ (4) were investigated. The structure of 3 contains $Cu^{II}$ centers with a square-pyramidal geometry, where the four basal sites are occupied by N(cyano) atoms of bridging [Au(CN)$_2$]$^-$ units and the apical site is occupied by an O-bound DMF molecule. Selected bond lengths and angles for 3 are listed in Table 4. The alternation of CuII centers and [Au(CN)$_2$]$^-$ units generates a 2-D square grid motif with all the DMF molecules pointing either above or below the plane of the sheet (FIG. 6(a)). This grid is similar to that observed in the blue Cu[Au(CN)$_2$]$_2$(DMSO)$_2$ complex (2) if one DMSO molecule was removed and the corrugation reduced. The layers stack on top of each other in an offset fashion, thereby disrupting any channels, and are held together by Au(1)-Au(1*$^a$) and Au(2)-Au(2*$^b$) interactions of 3.3050(12) Å and 3.1335(13) Å (FIG. 6(b)).

Crystal Structure of Cu[Au(CN)$_2$]$_2$(pyridine)$_2$, 4. The structure of 4 is similar to that of 3, except that the $Cu^{II}$ centers are surrounded by two solvent molecules, generating octahedrally coordinated metals. The axial sites and two of the equatorial sites are occupied by N(cyano) atoms of bridging [Au(CN)$_2$]$^-$ units. Pyridine molecules occupy the two other equatorial sites. Selected bond lengths and angles for 4 are listed in Table 5. As observed for 3, infinite 2-D layers are obtained (FIGS. 7(a) and (b)). No aurophilic interactions are present between the Au atoms of neighboring sheets, but π-π interactions of ~3.4 Å are found between stacked pyridine rings of adjoining sheets. Thus, the square-grid array present in 2 and 3 is maintained but in this case the sheets are completely flat, as opposed to the corrugated array found in 2. The 180° disposition of the pyridine rings (vs. the cis orientation of the DMSO molecules in 2) also serves to separate the sheets, disrupting potential intersheet Au—Au interactions.

Solvent free Cu[Au(CN)$_2$]$_2$, 6. The green-brown solvent-free complex, Cu[Au(CN)$_2$]$_2$ (6), was also prepared by thermally removing in vacuo the water molecules from 5. Changes in the powder X-ray diffractogram and in the $v_{CN}$ peaks of 6 indicate that some rearrangement in the framework occurred. The IR spectrum only shows one stretching frequency (2191 cm$^{-1}$), indicating that all CN groups are in a similar environment, reminiscent of the Cu[Au(CN)$_2$]$_2$(DMF) structure. This is also comparable with the results published for the Mn[Au(CN)$_2$]$_2$(H$_2$O)$_2$[40] and the Co[Au(CN)$_2$]$_2$(DMF)$_2$[41] systems (which show stretches at 2150 and 2179 cm$^{-1}$ respectively). In these two coordination polymers, the M[Au(CN)$_2$]$_2$ unit (M=Mn or Co) forms 2-D square grids, with solvent molecules hanging above and below the plane of the sheet. Although the three-dimensional topology of Cu[Au(CN)$_2$]$_2$ is not known, it likely forms a similar 2-D square grid network with all N(cyano) atoms equatorially bound to a square planar Cu$^{II}$ center (FIG. 8), as would be generated by structurally erasing the DMF molecule from 3. The Cu[Au(CN)$_2$]$_2$ system was found to be only slightly porous by N$_2$-adsorption measurements, suggesting that the 2-D sheets stack in an offset fashion, likely with significant aurophilic interactions, thereby blocking channel formation. Despite this, solvents are still taken up by this system to yield the same Cu[Au(CN)$_2$]$_2$(solvent)$_x$ complexes.

Concentration-controlled synthesis of structural isomers of coordination polymers Results obtained by X-ray crystallography and elemental analysis indicate that 1 and 2 of this Example are true polymorphs or supramolecular isomers, as opposed to pseudopolymorphs that differ by incorporation of varying amounts or identities of co-crystallized solvent molecules.[3,4] As mentioned above, many factors contribute to the preferential formation of one polymorph over another and it can often be a challenge to control the synthesis of a desired isomer.[3-7] Varying crystallization conditions, such as solvent type, starting materials, temperature and concentration are often important to ensure generation of just one polymorph. For example, crystallizing Ni[Au(CN)$_2$]$_2$(en)$_2$ (en=1,2-ethylenediamine) from [Ni(en)$_3$]Cl$_2$.2H$_2$O or [Ni(en)$_2$Cl$_2$] generates molecular and 1-dimensional polymorphic materials respectively.[34] Also, it has been shown that metastable polymorphs can be obtained by rapid crystallization from a supersaturated solution, e.g., via a fast drop in temperature.[6,42] For example, {Cu[N(CN)$_2$]$_2$(pyrazine)}$_n$ forms green/blue and blue polymorphs when crystallized from concentrated and dilute solution respectively.[43]

Similarly, in the Cu[Au(CN)$_2$]$_2$(DMSO)$_2$ system described in this Example, if the total concentration of reagents is below 0.2 M, 1 is formed, while 2 is obtained exclusively from >0.5 M solutions. The concentration-controlled synthesis of structural isomers of coordination polymers is uncommon relative to examples with molecular systems.[43,44] This concentration dependence suggests that green 1 is the thermodynamic product, while blue 2, which rapidly precipitates from solution, is likely a kinetic product. The fact that Cu[Au(CN)$_2$]$_2$(H$_2$O)$_2$ converts exclusively to the green polymorph 1 when adsorbing DMSO is further evidence that 1 is the most energetically favorable polymorph. Interestingly, the density of thermodynamically preferred 1 is actually lower than that of 2. This surprising situation has been observed in other polymolphs.[8] Although it is unclear if this result can be attributed to entropic or enthalpic contributions, it is conceivable that the formation of shorter Au—Au bonds in 1 relative to 2 could be an important energetic factor.

Metal-ligand superstructures It has been recognized that a system does not need to be porous in order to undergo guest uptake.[45] For example, a flexible metal-ligand superstructure can dynamically adapt in order to accommodate a variety of potential guests.[45-51] In this light, the Jahn-Teller influenced flexible coordination sphere and the greater lability of Cu$^{II}$ compared with other transition metals are likely important features of the Cu[Au(CN)$_2$]$_2$(solvent)$_x$ system. The related Mn[Au(CN)$_2$]$_2$(H$_2$O)$_2$ and Co[Au(CN)$_2$]$_2$(DMF)$_2$ systems previously reported form more rigid frameworks.[40,41] For these two systems, thermal treatment is required to remove the guest molecules and yield compounds exhibiting zeolitic properties. The lability of Cu$^{II}$ in the system of the present invention facilitates the reversible exchange of adsorbed solvent molecules without any thermal treatment required. It also likely increases the flexibility of the framework by allowing the breaking and the reformation of Cu—N(cyano) bonds, thereby adapting to the solvent guest present. Gold-gold interactions are probably present in all the Cu[Au(CN)$_2$]$_2$(solvent)$_x$ complexes and help to stabilize the 3D-network as solvent exchange takes place.

Taking into account the varied structures of the Cu[Au(CN)$_2$]$_2$(solvent)$_x$ complexes, several modes of flexibility within the fundamental structural framework, i.e. the two-dimensional square-grid network of the Cu[Au(CN)$_2$]$_2$ moiety (FIG. 8), can be identified. Firstly, the 2-D square-grid can lie entirely flat, as in the bis-pyridine or mono-DMF complexes 3 and 4, or it can buckle to generate a corrugated 2-D array, as observed in the blue bis-DMSO polymorph 2. The extent of this corrugation can even force the partial fragmentation of the square array via the breaking of one Cu—N(cyano) bond, as observed in the green bis-DMSO polymorph 1. Such fragmentation is probably also present in the Cu[Au(CN)$_2$]$_2$(NH$_3$)$_4$ complex (9); the Cu$^{II}$ center in 9 is likely still octahedral, with two Cu—N(cyano) bonds (out of four in the fundamental square-grid structure) breaking completely to make way for two additional NH$_3$ ligands, thereby disrupting the 2-D array. Another mode of flexibility lies in the ability of the Cu$^{II}$ center to readily alternate between being five- and six-coordinate, as well as accessing a range of five-coordinate geometries. This adaptability is independent of the extent of corrugation: five-coordinate Cu$^{II}$ centers are found in both flat 3 and corrugated 1 while six-coordinate centers are present in both flat 4 and corrugated 2. Finally, the Jahn-Teller distortions endemic to Cu$^{II}$ complexes yield a third mode of flexibility: the arrangement of equatorial/axial or basal/apical N(cyano) ligands and donor solvents. Again, this pliability is independent of the extent of corrugation: both the five-coordinate DMF complex 3 and six-coordinate bis-pyridine complex 4 contain flat Cu[Au(CN)$_2$]$_2$ square-grids, but in 3 the N(cyano) ligands are all basal (and therefore roughly identical in length) while in 4 two N(cyano) ligands are equatorial and two are axial, leading to significantly different Cu—N(cyano) bond lengths. This form of structural flexibility is particularly important since substantially different IR signatures in the cyanide region are generated depending on the N(cyano) bonding arrangement in the system. Of course, all three modes of flexibility work in concert to generate the adaptable, dynamic network solid that is ultimately able to bind and sense different donor solvents.

The source of the vapochromism in the Cu[Au(CN)$_2$]$_2$(solvent)$_x$ system differs from that of other Au$^I$-containing systems.[9-12] Cu[Au(CN)$_2$]$_2$(solvent)$_x$ shows vapochromism in the visible since each donor solvent molecule that is adsorbed binds to the Cu$^{II}$ center and modifies differently the crystal field splitting. As a consequence, the colour of the vapochromic compound changes as the d-d absorption bands shift with donor. In addition to donor identity, the resulting coordination number (five or six) and specific geometry of the copper center also influences the colour of the complexes by altering the splitting of the d-orbitals.

The [Au(CN)$_2$]$^-$ unit is also a key component of this system since it telegraphs the changes in solvent bound to the Cu$^{II}$ centers via the $v_{CN}$ stretch. Each Cu[Au(CN)$_2$]$_2$(solvent)$_x$ has a different IR signature since every VOC modifies in a different manner the electron density distribution around the Cu$^{II}$ center. This influences the amount of π-back bonding from the Cu$^{II}$ center to the CN group, which in turn is observed in the IR spectrum due to the change in vibration frequency.[27] Also, the number of bands observed is related to the symmetry and coordination number of the Cu$^{II}$ centers, as described in detail above.

In summary, it has been illustrated in this Example that, despite their different solid-state structures, the two Cu[Au $(CN)_2]_2(DMSO)_2$ polymorphs exhibit the same vapochromic behaviour with respect to sorption of analytes such as VOCs. The use of $[Au(CN)_2]^-$ as a building block is important to the function of this vapochromic coordination polymer. First, it provides the very sensitive CN reporter group that can allow IR-identification of the solvent adsorbed in the materials. Also, Au—Au interactions via the $[Au(CN)_2]^-$ units increase the structural dimensionality of the system in most cases and probably help provide stabilization points for the flexible $Cu[Au(CN)_2]_2$ framework.

Example 2.0

2.1 $Zn[Au(CN)_2]_2(solvent)_x$ System

Synthesis of $Zn[Au(CN)_2]_2(DMSO)_2$. To a 1 mL DMSO solution of $Zn(ClO_4)_2(H_2O)_6$ (0.032 g, 0.086 mmol) was added $KAu(CN)_2$ (0.050 g, 0.173). Slow evaporation yielded crystals of $Zn[Au(CN)_2]_2(DMSO)_2$. Anal. Calcd. for $C_8H_{12}N_4Au_2O_2S_2Zn$: C, 13.35; H, 1.68; N, 7.79%. Found: C, 13.50; H, 1.72; N, 8.04%. IR (KBr, cm$^{-1}$) 3009 (in), 2919(m), 2849(w), 2186(s), 2175(s), 1409(m), 1314(m), 1299(m), 1031(m), 1013(s), 1005(s), 957(m), 710(w).

Although the structure of a solvent-free $Zn[Au(CN)_2]_2$ polymer is known, it is believed that no luminescence or analyte binding properties have previously been reported. FIG. 9 consists of photographs showing changes in luminescence in a $Zn[Au(CN)_2]_2(analyte)_x$ system under room light (top) and ultraviolet light (bottom). From left to right the analyte is None, $NH_3$, pyridine, $CO_2$ and DMSO. As in Example 1.0 above, the cyanide-IR changes are also dramatic and distinctive for each analyte.

The zinc-based polymer described herein appears to bind $CO_2$: Anal. Calcd. for $C_5N_4Au_2O_2Zn$: C, 9.89; H, 0.00; N, 9.22%. Found: C, 9.73; H, 0.00; N, 9.32%. IR (KBr, cm$^{-1}$): 2192 (s).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

TABLE 2

Selected bond lengths (Å) and angles (°) for $Cu[Au(CN)_2]_2(DMSO)_2$ (1).

| | | | |
|---|---|---|---|
| Au(1)-Au(2) | 3.22007(5) | Cu(1)-N(2) | 2.107(18) |
| Cu(1)-O(1) | 1.949(7) | Cu(1)-N(3) | 1.965(11) |
| O(1)-Cu(1)-O(1*) | 167.0(6) | Cu(1)-N(2)-C(2) | 180 |
| O(1)-Cu(1)-N(2) | 96.5(3) | Cu(1)-N(3)-C(3) | 178.6(12) |
| O(1)-Cu(1)-N(3) | 87.3(4) | Au(2)-Au(1)-Au(2) | 171.73(3) |
| O(1*)-Cu(1)-N(3) | 88.4(4) | Au(1)-N(1)-C(1) | 180 |
| N(2)-Cu(1)-N(3) | 109.5(4) | Au(1)-N(2)-C(2) | 180 |
| N(3)-Cu(1)-N(3*) | 140.9(8) | Au(2)-N(3)-C(3) | 178.9(12) |
| Cu(1)-O(1)-S(1) | 127.2(6) | C(1)-Au(1)-C(2) | 180 |

Symmetry transformations:
*−x + 1, y, −z + 1/2;
'−x + 1/2, −y − 5/2, z + 1.

TABLE 3

Selected bond lengths (Å) and angles (°) for $Cu[Au(CN)_2]_2(DMSO)_2$ (2)

| | | | |
|---|---|---|---|
| Au(1)-Au(2) | 3.419(3) | Au(3)...Au(4) | 3.592(4) |
| Cu(1)-O(1) | 2.02(3) | Cu(2)-O(3) | 1.97(3) |
| Cu(1)-O(2) | 1.95(3) | Cu(2)-O(4) | 2.29(3) |
| Cu(1)-N(11) | 2.42(4) | Cu(2)-N(12) | 2.11(4) |
| Cu(1)-N(21) | 1.97(4) | Cu(2)-N(22) | 2.37(5) |
| Cu(1)-N(31) | 2.42(4) | Cu(2)-N(32) | 2.03(5) |
| Cu(1)-N(41) | 1.99(4) | Cu(2)-N(42) | 2.00(5) |
| O(1)-Cu(1)-O(2) | 95.2(12) | O(3)-Cu(2)-O(4) | 93.0(12) |
| O(1)-Cu(1)-N(11) | 85.9(12) | O(3)-Cu(2)-N(12) | 87.8(15) |
| O(2)-Cu(1)-N(11) | 86.4(12) | O(4)-Cu(2)-N(12) | 87.0(14) |
| N(11)-Cu(2)-N(21) | 92.7(14) | N(12)-Cu(2)-N(22) | 92.3(16) |
| N(11)-Cu(2)-N(31) | 172.7(13) | N(12)-Cu(2)-N(32) | 172.0(17) |
| N(11)-Cu(2)-N(41) | 92.6(14) | N(12)-Cu(2)-N(42) | 95.2(17) |
| N(21)-Cu(2)-N(31) | 92.6(15) | N(22)-Cu(2)-N(32) | 91.4(17) |
| N(21)-Cu(2)-N(41) | 90.7(15) | N(22)-Cu(2)-N(42) | 91.2(17) |
| N(31)-Cu(2)-N(41) | 92.3(14) | N(32)-Cu(2)-N(42) | 91.8(18) |
| Cu(1)-O(1)-S(1) | 124.9(17) | Cu(2)-O(3)-S(3) | 125.4(20) |
| Cu(1)-O(2)-S(2) | 124.4(19) | Cu(2)-O(4)-S(4) | 127.9(18) |
| Cu(1)-N(11)-C(11) | 169.2(45) | Cu(2)-N(12)-C(12) | 163.5(50) |
| Cu(1)-N(21)-C(21) | 163.5(41) | Cu(2)-N(22)-C(22) | 159.5(46) |
| Cu(1)-N(31)-C(31) | 161.7(43) | Cu(2)-N(32)-C(32') | 174.6(45) |
| Cu(1)-N(41)-C(41) | 166.4(33) | Cu(2)-N(42)-C(42) | 170.0(45) |
| C(11)-Au(1)-C(12) | 172.7(25) | C(31)-Au(3)-C(32) | 172.6(18) |
| C(21)-Au(2)-C(22*) | 175.9(23) | C(41*[b])-Au(4)-C(42) | 177.9(20) |
| Au(1)-C(11)-N(11) | 175.8(50) | Au(3)-C(31)-N(31) | 171.0(39) |

TABLE 1

Crystallographic Data and Structural Refinement Details

| | 1 (Green) | 2 (Blue) | 3 | 4 |
|---|---|---|---|---|
| empirical formula | $C_8H_{12}N_4Au_2CuO_2S_2$ | $C_8H_{12}N_4Au_2CuO_2S_2$ | $C_7H_7N_5Au_2CuO$ | $C_{14}H_{10}N_6Au_2Cu$ |
| fw | 717.82 | 717.82 | 634.65 | 719.76 |
| Crystal system | monoclinic | triclinic | monoclinic | monoclinic |
| Space group | C2/c | P$\bar{1}$ | C2/c | P2$_1$/c |
| a, Å | 11.5449(15) | 7.874(7) | 12.8412(10) | 7.3438(7) |
| b, Å | 14.191(4) | 12.761(11) | 14.5056(8) | 14.1201(10) |
| c, Å | 11.5895(12) | 16.207(13) | 13.9932(9) | 8.2696(6) |
| α, deg | 90 | 89.61(7) | 90 | 90 |
| β, deg | 112.536(9) | 82.29(7) | 96.064(3) | 94.082(3) |
| γ, deg | 90 | 88.57(7) | 90 | 90 |
| V, Å$^3$ | 1753.8(6) | 1613.2(24) | 2591.9(3) | 855.34(12) |
| Z | 4 | 2 | 8 | 4 |
| T, K | 293 | 293 | 293 | 293 |
| λ, Å | 0.70930 | 1.54180 | 1.54180 | 1.54180 |
| $\rho_{calcd}$, g·cm$^{-3}$ | 2.719 | 2.955 | 3.253 | 2.794 |
| μ, mm$^{-1}$ | 18.079 | 37.500 | 43.542 | 33.103 |
| $R_1^a$ (I > xσ(I))$^b$ | 0.042 | 0.062 | 0.032 | 0.028 |
| $wR_2^a$ (I > xσ(I))$^b$ | 0.047 | 0.082 | 0.046 | 0.040 |
| Goodness of fit | 2.20 | 1.38 | 0.93 | 1.00 |

[a]Function minimized $\Sigma w(|F_o| - |F_c|)^2$ where $w^{-1} = \sigma^2(F_o) + 0.0001 F_o^2$, $R = \Sigma||F_o| - |F_c||/\Sigma|F_o|$, $R_w = [\Sigma w|F_o| - |F_c|)^2/\Sigma w|F_o|^2]^{1/2}$.
[b]For 1, x = 2.5; for 2, 3 and 4, x = 3.

TABLE 3-continued

Selected bond lengths (Å) and angles (°) for Cu[Au(CN)$_2$]$_2$(DMSO)$_2$ (2)

| | | | |
|---|---|---|---|
| Au(1)-C(12)-N(12) | 175.3(58) | Au(3)-C(32)-N(32$^{\prime b}$) | 175.6(49) |
| Au(2)-C(21)-N(21) | 173.2(42) | Au(4*$^b$)-C(41)-N(41) | 174.2(38) |
| Au(2*)-C(22)-N(22) | 175.2(56) | Au(4)-C(42)-N(42) | 170.1(46) |

Symmetry transformations:
*−x + 1, −y + 1, −z + 1;
*$^b$−x + 1, −y, −z + 1;
'x + 2, y, z − 1;
'$^b$x − 2, y, z + 1.

TABLE 4

Selected bond lengths (Å) and angles (°) for Cu[Au(CN)$_2$]$_2$(DMF) (3).

| | | | |
|---|---|---|---|
| Au(1)-Au(1*$^a$) | 3.3050(12) | Cu(1)-N(2) | 1.990(11) |
| Au(2)-Au(2*$^b$) | 3.1335(13) | Cu(1)-N(3) | 1.961(10) |
| Cu(1)-O(1) | 2.202(12) | Cu(1)-N(4'$^b$) | 1.982(10) |

TABLE 5

Selected bond lengths (Å) and angles (°) for Cu[Au(CN)$_2$]$_2$(pyridine)$_2$ (4).

| | | | |
|---|---|---|---|
| Cu(1)-N(1) | 2.016(9) | Cu(1)-N(3) | 2.007(7) |
| Cu(1)-N(2*$^a$) | 2.532(9) | | |
| N(1)-Cu(1)-N(2*$^a$) | 89.5(4) | C(2)-Au(1)-C(1) | 177.8(4) |
| N(1')-Cu(1)-N(2*$^a$) | 90.5(4) | Cu(1)-N(1)-C(1) | 169.7(9) |
| N(1)-Cu(1)-N(3) | 90.0(3) | Cu(1*$^b$)-N(2)-C(2) | 173.3(9) |
| N(1)-Cu(1)-N(3') | 90.0(3) | Au(1)-C(1)-N(1) | 177.9(9) |
| N(2*$^a$)-Cu(1)-N(3) | 90.4(3) | Au(1)-C(2)-N(2) | 177.2(11) |
| N(2*$^a$)-Cu(1)-N(3') | 89.6(3) | | |

Symmetry transformations:
*$^a$x − 1, −y + 1/2, z − 1/2;
*$^b$x + 1, −y + 1/2, z + 1/2;
'−x + 1, −y, −z + 1.

TABLE 6

Maximum Solid-state Visible Reflectance (nm) and Cyanide $\nu_{CN}$ Absorptions (cm$^{-1}$) for Different Cu[Au(CN)$_2$]$_2$(solvent)$_x$ Complexes

| | Complex | Maximum visible reflectance | $\nu_{CN}$ absorption(s) From solution | From adsorption$^a$ |
|---|---|---|---|---|
| (1) | Cu[Au(CN)$_2$]$_2$(DMSO)$_2$ | 550 ± 7 | 2183(s), 2151(s) | 2184(s), 2151(s) (from 5) |
| (2) | Cu[Au(CN)$_2$]$_2$(DMSO)$_2$ | 535 ± 15 (broad) | 2206(m), 2193(s), 2175(m), 2162(m) | — |
| (3) | Cu[Au(CN)$_2$]$_2$(DMF) | 498 ± 7 | 2199(s) | 2199 (s) |
| (4) | Cu[Au(CN)$_2$]$_2$(pyridine)$_2$ | 480 ± 15 (broad) | 2179(m), 2167(s), 2152(m), 2144(m) | 2179(m), 2167(s), 2152(m), 2144(m) |
| (5) | Cu[Au(CN)$_2$]$_2$(H$_2$O)$_2$ | 535 ± 5 | 2217(s), 2194(w), 2172(s) | 2217(s), 2194(w), 2171(s) (from 1) 2216(s), 2196(w), 2171(s) (from 2) |
| (6) | Cu[Au(CN)$_2$]$_2$ | 560 ± 20 (v. broad) | 2191(s) | — |
| (7) | Cu[Au(CN)$_2$]$_2$(CH$_3$CN)$_2$ | — | 2297(w), 2269(w), 2191(s) | |
| (8) | Cu[Au(CN)$_2$]$_2$(dioxane)(H$_2$O) | 505 ± 15 (broad) | 2201(s), 2172(w) | 2200(s), 2174 (w) |
| (9) | Cu[Au(CN)$_2$]$_2$(NH$_3$)$_4$ | 433 ± 7 | — | 2175(m), 2148(s) |

$^a$All solvent adducts were made from 2 unless specified

TABLE 4-continued

Selected bond lengths (Å) and angles (°) for Cu[Au(CN)$_2$]$_2$(DMF) (3).

| | | | |
|---|---|---|---|
| Cu(1)-N(N') | 1.958(10) | O(1)-C(5) | 1.202(17) |
| N(1'$^a$)-Cu(1)-N(2) | 89.8(4) | C(1)-Au(1)-C(2) | 176.0(6) |
| N(1'$^a$)-Cu(1)-N(3) | 88.7(5) | C(3)-Au(2)-C(4) | 175.4(6) |
| N(4'$^b$)-Cu(1)-N(2) | 89.6(5) | Cu(1'$^c$)-N(1)-C(1) | 170.1(12) |
| N(4'$^b$)-Cu(1)-N(3) | 89.3(5) | Cu(1)-N(2)-C(2) | 172.7(14) |
| N(1'$^a$)-Cu(1)-N(4'$^b$) | 166.7(5) | Cu(1)-N(3)-C(3) | 170.8(12) |
| N(2)-Cu(1)-N(3) | 169.2(5) | Cu(1'$^d$)-N(4)-C(4) | 172.1(12) |
| O(1)-Cu(1)-N(1'$^a$) | 95.1(5) | Au(1)-C(1)-N(1) | 174.9(13) |
| O(1)-Cu(1)-N(2) | 98.3(5) | Au(1)-C(2)-N(2) | 177.8(14) |
| O(1)-Cu(1)-N(3) | 92.4(5) | Au(2)-C(3)-N(3) | 174.3(13) |
| O(1)-Cu(1)-N(4'$^b$) | 98.1(5) | Au(2)-C(4)-N(4) | 177.5(16) |
| Cu(1)-O(1)-C(5) | 125.4(13) | | |

Symmetry transformations:
*$^a$−x − 1, y, −z + 3/2;
*$^b$−x − 1, −y, −z + 1/2;
'$^a$x, −y, z − 1/2;
'$^b$x, −y − 1, z + 1/2;
'$^c$x, −y, z + 1/2;
'$^d$x, −y − 1, z − 1/2.

TABLE 7

Thermal Decomposition of Different Cu[Au(CN)$_2$]$_2$(solvent)$_x$ Complexes

| Complex | Temperature (° C.) | Decomposition product or lost fragment | Weight (%) calcd | found |
|---|---|---|---|---|
| 3 | 195-280 | −DMF | 11.5 | 13.6 |
| | 310-355 | −2 C$_2$N$_2$ + O | 13.8 | 11.5 |
| | 400 | CuO + 2 Au | 74.6 | 73.9 |
| 4 | 155-190 | −1 pyridine | 11.0 | 10.9 |
| | 210-260 | −1 pyridine | 11.0 | 12.6 |
| | 310-330 | −2 C$_2$N$_2$ + O | 12.2 | 9.2 |
| | 400 | CuO + 2 Au | 65.8 | 66.4 |
| 5 | 140-180 | −2 water | 6.0 | 5.5 |
| | 260-380 | −2 C$_2$N$_2$ + O | 14.7 | 13.5 |
| | 400 | CuO + 2 Au | 79.2 | 81.5 |
| 6 | 200-350 | −2 C$_2$N$_2$ + O | 15.2 | 15.5 |
| | 400 | CuO + 2 Au | 81.7 | 80.9 |
| 8 | 150-280 | −dioxane − H$_2$O | 15.9 | 17.5 |
| | 290-330 | −2 C$_2$N$_2$ + O | 13.2 | 10.3 |
| | 400 | CuO + 2 Au | 70.9 | 71.1 |

TABLE 7-continued

Thermal Decomposition of Different Cu[Au(CN)$_2$]$_2$(solvent)$_x$ Complexes

| Complex | Temperature (° C.) | Decomposition product or lost fragment | Weight (%) calcd | found |
|---|---|---|---|---|
| 9 | 50-95 | −1 NH$_3$ | 2.7 | 2.8 |
|  | 115-220 | −3 NH$_3$ | 8.1 | 7.5 |
|  | 280-350 | −2 C$_2$N$_2$ + O | 14.0 | 13.7 |
|  | 400 | CuO + 2 Au | 75.2 | 74.4 |

REFERENCES (1) Janiak, C. *J. Chem. Soc., Dalton Trans.* 2003, 2781-2804.
(2) James, S. L. *Chem. Soc. Rev.* 2003, 32, 276-288.
(3) Moulton, B.; Zaworotko, M. *J. Chem. Rev.* 2001, 101, 1629-1658.
(4) Batten, S. R.; Murray, K. S. *Aust. J. Chem.* 2001, 54, 605-609.
(5) Dunitz, J. D.; Bernstein, J. *Acc. Chem. Res.* 1995, 28, 193.
(6) Bernstein, J. *Polymorphism in Molecular Crystals*; Oxford University Press: Oxford, 2002.
(7) Braga, D.; Grepioni, F. *Chem. Soc. Rev.* 2000, 29, 229-238.
(8) Heintz, R. A.; Zhao, H.; Ouyang, X.; Grandinetti, G.; Cowen, J.; Dunbar, K. R. *Inorg. Chem.* 1999, 38, 144.
(9) White-Morris, R. L.; Olmstead, M. M.; Jiang, F.; Tinti, D. S.; Balch, A. L. *J. Am. Chem. Soc.* 2002, 124, 2327-2336.
(10) Mansour, M. A.; Connick, W. B.; Lachicotte, R. J.; Gysling, H. J.; Eisenberg, R. *J. Am. Chem. Soc.* 1998, 120, 1329-1330.
(11) Rawashdeh-Omary, M. A.; Omary, M. A.; Fackler, J. P., Jr.; Galassi, R.; Pietroni, B. R.; Burini, A. *J. Am. Chem. Soc.* 2001, 123, 9689-9691.
(12) Fernandez Eduardo, J.; Lopez-De-Luzuriaga Jose, M.; Monge, M.; Olmos, M. E.; Perez, J.; Laguna, A.; Mohamed Ahmed, A.; Fackler Jolm, P., Jr. *J. Am. Chem. Soc.* 2003, 125, 2022-2023.
(13) Exstrom, C. L.; Sowa, J. R., Jr.; Daws, C. A.; Janzen, D.; Malm, K. R.; Moore, G. A.; Stewart, F. F. *Chem. Mater.* 1995, 7, 15-17.
(14) Drew, S. M.; Janzen, D. E.; Buss, C. E.; MacEwan, D. I.; Dublin, K. M.; Mann, K. R. *J. Am. Chem. Soc.* 2001, 123, 8414-8415.
(15) Beauvais, L. G.; Shores, M. P.; Long, J. R. *J. Am. Chem. Soc.* 2000, 122, 2763-2772.
(16) Buss, C. E.; Anderson, C. E.; Pomije, M. K.; Lutz, C. M.; Britton, D.; Mann, K. R. *J. Am. Chem. Soc.* 1998, 120, 7783-7790.
(17) Bariain, C.; Matias, I. R.; Romeo, I.; Gamido, J.; Laguna, M. *Appl. Phys. Lett.* 2000, 77, 2274-2276.
(18) Kunugi, Y.; Mann, K. R.; Miller, L. L.; Exstrom, C. L. *J. Am. Chem. Soc.* 1998, 120, 589-590.
(19) Kunugi, Y.; Miller, L. L.; Mann, K. R.; Pomije, M. K. *Chem. Mater.* 1998, 10, 1487-1489.
(20) Kahn, O. *Molecular Magnetism*; VCH: Weinheim, 1993.
(21) Gabe, E. J.; White, P. S.; Enright, G. D. *DIFRACA Fortran 77 Control Routine for 4-Circle Diffractometers*; N. R. C.: Ottawa, 1995.
(22) Gabe, E. J.; LePage, Y.; Charland, J.-P.; Lee, F. L.; White, P. S. *J. Appl. Crystallogr.* 1989, 22, 384.
(23) Higashi, T. *Program for Absorption Correction*; Rigaku Corporation: Tokyo, Japan, 1999.
(24) Watkin, D. J.; Prout, C. K.; Carruthers, J. R.; Betteridge, P. W.; Cooper, R. I. *CRYSTALS Issue* 11 Chemical Crystallography Laboratory, University of Oxford, Oxford, England, 1999.
(25) Farrugia, L. J. *J. Appl. Crystallogr.* 1997, 30, 565.
(26) Fenn, T. D.; Ringe, D.; Petsko, J. *Appl Crystallogr.* 2003, 36, 944-947. (Persistence of Vision Raytracing: http://www.povray.org).
(27) Dunbar, K. R.; Heintz, R. A. *Prog. Inorg. Chem.* 1997, 45, 283-391.
(28) Addison, A. W.; Rao, T. N.; Reedijk, J.; Van Rijn, J.; Verschoor, G. C. *J. Chem. Soc., Dalton Trans.* 1984, 1349-1356.
(29) Schmidbaur, H. *Chem. Soc. Rev.* 1995, 24, 391.
(30) Carlin, R. L. *Magnetochemistry*; Springer-Verlag: Berlin, Heidelberg, Germany, 1986.
(31) Leznoff, D. B.; Xue, B.-Y.; Patrick, B. O.; Sanchez, V.; Thompson, R. C. *Chem. Commun.* 2001, 259-260.
(32) Leznoff, D. B.; Xue, B. Y.; Stevens, C. L.; Storr, A.; Thompson, R. C.; Patrick, B. O. *Polyhedron* 2001, 20, 1247-1254.
(33) Leznoff, D. B.; Xue, B.-Y.; Batchelor, R. J.; Einstein, F. W. B.; Patrick, B. O. *Inorg. Chem.* 2001, 40, 6026-6034.
(34) Colacio, E.; Lloret, F.; Kivekaes, R.; Suarez-Varela, J.; Sundberg, M. R.; Uggla, R. *Inorg. Chem.* 2003, 42, 560-565.
(35) Chomic, J.; Cernak, J. *Thermochim. Acta* 1985, 93, 93.
(36) Noro, S.-i.; Kitaura, R.; Kondo, M.; Kitagawa, S.; Ishii, T.; Matsuzaka, H.; Yamashita, M. *J. Am. Chem. Soc.* 2002, 124, 2568-2583.
(37) Seld, K. *Chem. Commun.* 2001, 1496-1497.
(38) Uemura, K.; Kitagawa, S.; Kondo, M.; Fukui, K.; Kitaura, R.; Chang, H.-C.; Mizutani, T. *Chem. Eur. J.* 2002, 8, 3586-3600.
(39) Eddaoudi, M.; Moler, D. B.; Li, H.; Chen, B.; Reineke, T. M.; O'Keeffe, M.; Yaghi, O. M. *Acc. Chem. Res.* 2001, 34, 319-330.
(40) Dong, W.; Zhu, L.-N.; Sun, Y.-Q.; Liang, M.; Liu, Z.-Q.; Liao, D.-Z.; Jiang, Z.-H.; Yan, S.-P.; Cheng, P. *Chem. Commun.* 2003, 2544-2545.
(41) Colacio, E.; Lloret, F.; Kivekaes, R.; Ruiz, J.; Suarez-Varela, J.; Sundberg, M. R. *Chem. Commun.* 2002, 592-593.
(42) Bernstein, J.; Davey, R. J.; Henck, J.-O. *Angew. Chem., Int. Ed.* 1999, 38, 3440.
(43) Jensen, P.; Batten, S. R.; Fallon, G. D.; Hockless, D. C. R.; Moubaraki, B.; Murray, K. S.; Robson, R. *J. Solid State Chem.* 1999, 145, 387-393.
(44) Barnett, S. A.; Blake, A. J.; Champness, N. R.; Wilson, C. *Chem. Commun.* 2002, 1640-1641.
(45) Atwood, J. L.; Barbour, L. J.; Jerga, A.; Schottel, B. L. *Science* 2002, 298, 1000-1002.
(46) Cote, A. P.; Shimizu, G. K. H. *Chem. Commun.* 2001, 251-252.
(47) Edgar, M.; Mitchell, R.; Slawin, A. M.; Lightfoot, P.; Wright, P. A. *Chem. Eur. J.* 2001, 7, 5168-5175.
(48) Miller, P. W.; Nieuwenhuyzen, M.; Xu, X.; James, S. L. *Chem. Commun.* 2002, 2008-2009.
(49) Lozano, E.; Nieuwenhuyzen, M.; James, S. L. *Chem. Eur. J.* 2001, 7, 2644-2651.
(50) Kitaura, R.; Fujimoto, K.; Noro, S.-i.; Kondo, M.; Kitagawa, S. *Angew. Chem., Int. Ed.* 2002, 41, 133-135.
(51) Côté, A. P.; Ferguson, M. J.; Khan, K. A.; Enright, G. D.; Kulynych, A. D.; Dalrymple, S. A.; Shimizu, G. K. H. *Inorg. Chem.* 2002, 41, 287-292.
(52) Assefa, Z.; Shankle, G.; Patterson, H. H.; Reynolds, R. *Inorg. Chem.* 1994, 33, 2187-2195.

(53) Stender, M.; White-Morris, R. L.; Olmstead, M. M.; Balch, A. L. *Inorg. Chem.* 2003, 42, 4504-4506.
(54) Daws, C. A.; Exstrom, C. L.; Sowa, J. R., Jr.; Mann, K. R. *Chem. Mater.* 1997, 9, 363-368.
(55) Exstrom, C. L.; Pomije, M. K.; Mann, K. R. *Chem. Mater.* 1998, 10, 942-945.
(56) Abrahams, S. C.; Zyontz, L. E.; Bernstein, J. L. *J. Chem. Phys.* 1982, 76, 5458.
(57) Abrahams, S. C.; Bernstein, J. L.; Liming a, R.; Eisenmann, E. T. *J. Chem. Phys.* 1980, 73, 4585.
(58) Hoskins, B. F.; Robson, R.; Scarlett, N. V. Y. *Angew. Chem. Int. Ed. Engl.* 1995, 34, 1203.
(59) Stier, A.; Range, K.-J. *Z Natuiforsch.* 1996, 51b, 698.
(60) Stier, A.; Range, K.-J. *Z Kristallogr.* 1997, 212, 51.
(61) Assefa, Z.; Staples, R. J.; Fackler, J. P., Jr.; Patterson, H. H.; Shankle, G. *Acta Crystallogr.* 1995, C51, 2527.
(62) Lefebvre, J.; Batchelor, R. J.; Leznoff, D. B. *J. Am. Chem. Soc.*, 2004, 126, 16117-16125.
(63) Shorrock, C. J.; Xue, B.-Y.; Kim, P. B.; Batchelor, R. J.; Patrick, B. O.; Leznoff, D. B. *Inorg. Chem.*, 2002, 41, 6743-53.
(64) Leznoff, D. B.; Draper, N. D.; Batchelor, R. J. *Polyhedron*, 2003, 22, 1735-1743.
(65) Draper, N. D.; Batchelor, R. J.; Sih, B. C.; Ye, Z.-G.; Leznoff, D. B. *Chem. Mater.*, 2003, 15, 1612-1616.
(66) Shorrock, C. J.; Jong, H.; Batchelor, R. J.; Leznoff, D. B. *Inorg Chem.*, 2003, 42, 3917-3924.
(67) Draper, N. D.; Batchelor, R. J.; Leznoff, D. B. *Crystal Growth and Design*, 2004, 4, 621-632.
(68) Draper, N. D.; Batchelor, R. J.; Aguiar, P. M.; Kroeker, S.; Leznoff, D. B. *Inorg. Chem.*, 2004, 43, 6557-6567.
(69) Katz, M. J.; Batchelor, R. J.; Leznoff, D. B. "Zn[Au(CN)$_2$]$_2$: A vapoluminescent material with two detection channels", Manuscript in preparation.

What is claimed is:

1. A method of vapochromically sensing the presence of an analyte, comprising:
   (a) providing a solid-state vapochromic structure comprising a coordination polymer having the chemical formula:

$$M_W[M'_X(Z)_Y]_N$$

wherein M and M' are the same or different metals capable of forming a coordination complex with the Z moiety, wherein at least one of the Z moiety comprises a bridging unit bound to M by a coordinate bond;
   Z is selected from the group consisting of halides, pseudohalides, thiolates, alkoxides and amides;
   W is between 1-6;
   X and Y between 1-9; and
   N is between 1-5;
   (b) exposing said solid-state vapochromic structure to said analtye; and
   (c) detecting any chromatic changes in said vapochromic structure.

2. A method of detecting an analyte comprising:
   (a) providing a sensor comprising a coordination polymer having the chemical formula:

$$M_W[M'_X(Z)_Y]_N$$

wherein M and M' are the same or different metals capable of forming a coordination complex with the Z moiety, wherein at least one of the Z moiety comprises a bridging unit bound to M by a coordinate bond;
   Z is selected from the group consisting of halides, pseudohalides, thiolates, alkoxides and amides
   W is between 1-6;
   X and Y between 1-9; and
   N is between 1-5;
   (b) exposing said polymer to a supply of said analyte; and
   (c) detecting any chromatic changes in said polymer resulting from exposure to said analyte.

3. The method as defined in claim 2, wherein said detecting comprises sensing any changes in the colour of said polymer.

4. The method as defined in claim 2, wherein said detecting comprises sensing any changes in the luminescence of said polymer.

5. The method as defined in claim 2, wherein said detecting comprises spectroscopically identifying any changes in the infrared signature of said polymer.

6. The method as defined in claim 5, wherein said spectroscopically identifying comprises detecting the number and position of $v_{CN}$ spectroscopic bands.

7. The method as defined in claim 2, wherein said chromatic changes are reversible.

8. The method as defined in claim 7, wherein said supply comprises different analytes and wherein steps (b) and (c) are dynamically repeated in respect of successive ones of said analytes.

9. The method as defined in claim 2, wherein M is Cu or Zn and wherein M' is Au.

10. The method as defined in claim 9, wherein said polymer is selected from the group consisting of Cu[Au(CN)$_2$]$_2$ and Zn[Au(CN)$_2$]$_2$.

11. The method as defined in claim 2, wherein said analyte is a volatile organic compound.

12. The method as defined in claim 2, wherein said analyte is a gas at room temperature and pressure.

13. The method as defined in claim 8, wherein said gas is CO and CO$_2$.

* * * * *